(12) United States Patent
Berkland et al.

(10) Patent No.: US 8,956,604 B2
(45) Date of Patent: *Feb. 17, 2015

(54) CONJUGATES COMPRISING AN N-OXIME BOND AND ASSOCIATED METHODS

(71) Applicant: University of Kansas, Lawrence, KS (US)

(72) Inventors: Cory Berkland, Lawrence, KS (US); Joshua Sestak, Lawrence, KS (US)

(73) Assignee: The University of Kansas, Lawrence, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/725,286

(22) Filed: Dec. 21, 2012

(65) Prior Publication Data

US 2013/0195791 A1 Aug. 1, 2013

Related U.S. Application Data

(63) Continuation-in-part of application No. PCT/US2011/041781, filed on Jun. 24, 2011.

(60) Provisional application No. 61/358,166, filed on Jun. 24, 2010.

(51) Int. Cl.
| | |
|---|---|
| *A61K 39/00* | (2006.01) |
| *A61K 47/48* | (2006.01) |
| *A61K 39/385* | (2006.01) |
| *C07B 43/00* | (2006.01) |

(52) U.S. Cl.
CPC .......... *A61K 39/0008* (2013.01); *A61K 39/385* (2013.01); *A61K 47/48092* (2013.01); *A61K 47/48176* (2013.01); *A61K 47/4823* (2013.01); *C07B 43/00* (2013.01); *A61K 47/489* (2013.01); *A61K 2039/627* (2013.01)
USPC ............... 424/78.27; 424/193.1; 435/69.7; 514/20.9; 514/640; 525/54.1; 530/345; 564/248; 564/278

(58) Field of Classification Search
USPC ............. 424/193.1, 78.27; 514/640; 564/248, 564/278
See application file for complete search history.

(56) References Cited

U.S. PATENT DOCUMENTS

| | | | |
|---|---|---|---|
| 5,880,270 A | 3/1999 | Berninger et al. | |
| 6,800,658 B2 | 10/2004 | Brugnara et al. | |
| 6,858,210 B1 | 2/2005 | Marquis et al. | |
| 2004/0224366 A1 | 11/2004 | Jones | |
| 2005/0169941 A1 | 8/2005 | Lees | |
| 2006/0058513 A1 | 3/2006 | Papisov | |
| 2008/0103091 A1 | 5/2008 | Siahaan | |
| 2010/0047225 A1* | 2/2010 | Zhu et al. ...................... | 424/94.3 |
| 2013/0216621 A1* | 8/2013 | Berkland et al. .............. | 424/489 |

OTHER PUBLICATIONS

Gajewiak et al., "Aminooxy Pluronics: Synthesis and Preparation of Glycosaminoglycan Adducts," 2006, Biomacromolecules, 7(6):1781-1789.*
Gauthier et al., "Peptide/protein-polymer conjugates: synthetic strategies and design concepts," 2008, Chem. Comm., 23:2591-2611.*
Heredia et al., "Aminooxy End-Functionalized Polymers Synthesized by ATRP for Chemoselective Conjugation to Proteins," 2007, Macromolecules, 40:4772-4779.*
Kirilmis, Cumhur, Synthesis and Antimicrobial Activity of Dinaphtho[2,1-b]furan-2-yl-methanone and Their Oxime Derivatives, Turk J Chem, 33 (2009), 375-384.
Sestak, Joshua Orion, Soluble Antigen Arrays utilize molecular and physical features to suppress Experimental Autoimmune Encephalomyelitis, Copyright 2011.
Demento et al., "Inflammasome-activating nanoparticles as modular systems for optimizing vaccine efficacy" May 18, 2009; 27(23):3013-21.

* cited by examiner

*Primary Examiner* — Jane C Osewcki
(74) *Attorney, Agent, or Firm* — Reed Smith LLP; Robert R. Riddle

(57) ABSTRACT

Conjugates comprising a N-oxime bond are disclosed. In one embodiment, a suitable conjugate is represented by the following Formula (I):

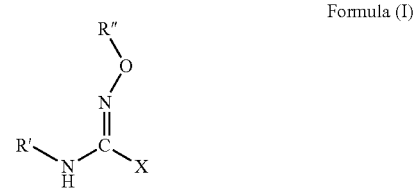

Formula (I)

wherein R' is derived from a compound comprising at least one reactive amide group, R" is derived from a compound comprising at least one reactive aminooxy group, and X is H, $C_nH_{(n+2)}$ or other atoms. Additional methods are also provided.

16 Claims, 17 Drawing Sheets

O-(carboxymethyl) hydroxylamine   Glucuronic Acid   *N-acetyl glucosamine*

(A) OCMH (B) N-acetyl Glucosamine (C) OCMH + N-acetylglucosamine Product 1H,1H-perfluoro-n-octyl acrylate (1,5-N-vinylformamido) ethyl ether N-vinylformamide Fluorescein-o-acrylate PVP, Vazo-52
———————→
EtOH, 60°C FIGURES 18A-18B
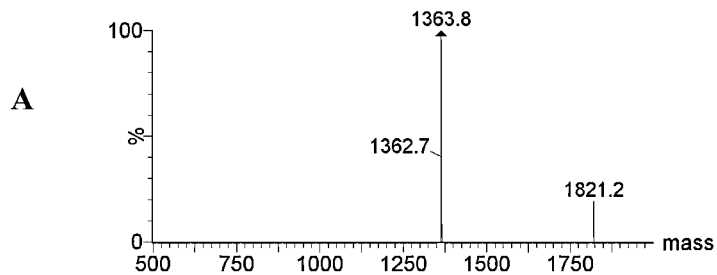
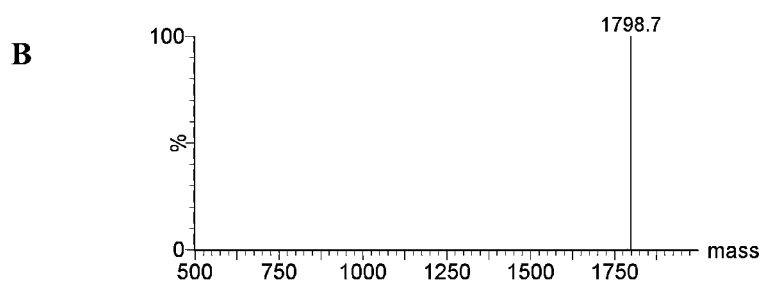
FIGURES 19A-19B
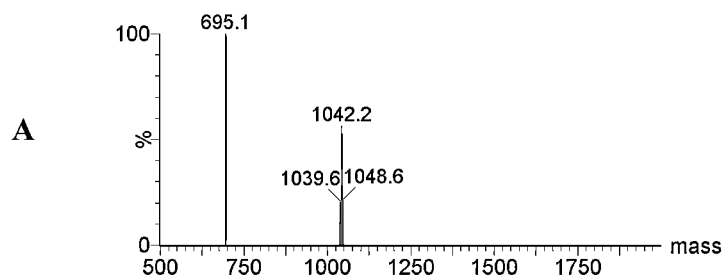
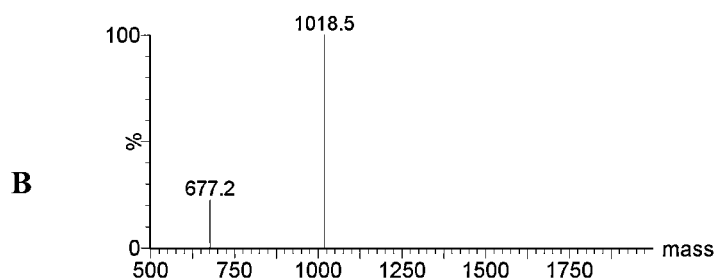

CONJUGATES COMPRISING AN N-OXIME BOND AND ASSOCIATED METHODS

CROSS REFERENCE TO RELATED APPLICATIONS

This application is a continuation-in-part of International Application No. PCT/US2011/41781, filed Jun. 24, 2011, which claims the benefit of U.S. Provisional Application No. 61/358,166, filed Jun. 24, 2010, the entire disclosures of which are incorporated herein by reference.

BACKGROUND

Oxime chemistry utilizing the highly specific reaction of an aminooxy group to an aldehyde or ketone has been previously established as a possible conjugation scheme. This conjugation scheme has been viewed favorably as the reaction between the aminooxy group and the aldehyde or ketone can occur rapidly and can proceed to high conversion, often without catalysts. In addition, aminooxy reactivity is significantly higher than primary amines, thus conferring the desired specificity for certain types of conjugations. However, one drawback to this approach has generally been the need to engineer the reactants to contain an aldehyde or ketone group and/or an aminooxy group.

Other conventional conjugation methods generally also have drawbacks in that they utilize reaction schemes that involve activating catalysts, include undesirable solvents, require modification of reactants, or necessitate the generation of intermediates. Additionally, conditions (e.g., pH, temperature, reagents) for many typical reactions may cause degradation of the reactants. Furthermore, low reactivity of the molecules or compounds, the addition of reactive groups, and use of unconventional solvents all contribute to complex reaction schemes, low reaction yields, or overall inefficiency.

SUMMARY

The present disclosure relates generally to conjugate compositions comprising an N-oxime bond and associated methods. More particularly, the present disclosure relates to conjugate compositions wherein a compound comprising at least one reactive amide group is reacted with a compound comprising at least one reactive aminooxy group to form a conjugate composition comprising at least one N-oxime bond.

In one embodiment, the present disclosure provides a method comprising: providing a first compound comprising at least one reactive amide group; providing a second compound comprising at least one reactive aminooxy group; and reacting the first compound comprising at least one reactive amide group with the second compound comprising at least one reactive aminooxy group to form a conjugate comprising at least one N-oxime bond.

In another embodiment, the present disclosure provides a composition comprising a conjugate represented by the following Formula (I):

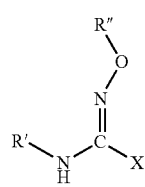

Formula (I)

wherein R' is derived from a compound comprising at least one reactive amide group, R" is derived from a compound comprising at least one reactive aminooxy group, and X is H, $C_nH_{(n+2)}$ or other atoms.

In another embodiment, the present disclosure provides a composition comprising a conjugate represented by the following Formula (II):

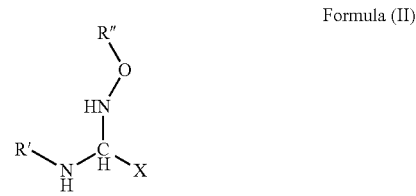

Formula (II)

wherein R' is derived from a compound comprising at least one reactive amide group, R" is derived from a compound comprising at least one reactive aminooxy group, and X is H, $C_nH_{(n+2)}$ or other atoms.

The features and advantages of the present invention will be readily apparent to those skilled in the art upon a reading of the description of the embodiments that follows.

DRAWINGS

Some specific example embodiments of the disclosure may be understood by referring, in part, to the following description and the accompanying drawings.

Figures 6A, 6B:
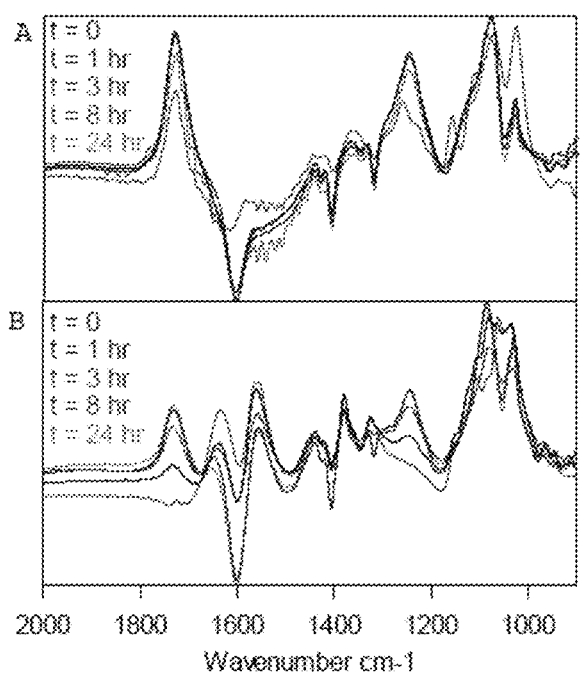

FIGS. 6A-6B are Fourier transform infrared (FTIR) spectra where (A) no change was shown over time in GLU mixed with OCMH and (B) changes in bonding environments for NAG reacted with OCMH were shown. The decrease in absorbance at 1650 and 1550 cm$^{-1}$ and the increase in absorbance at ~1750 and 1250 cm$^{-1}$ over time are indicative of the loss of the amide environment and the appearance of carboxylic acid and N-oxime environments due to the reaction of NAG with OCMH.

Figure 7:
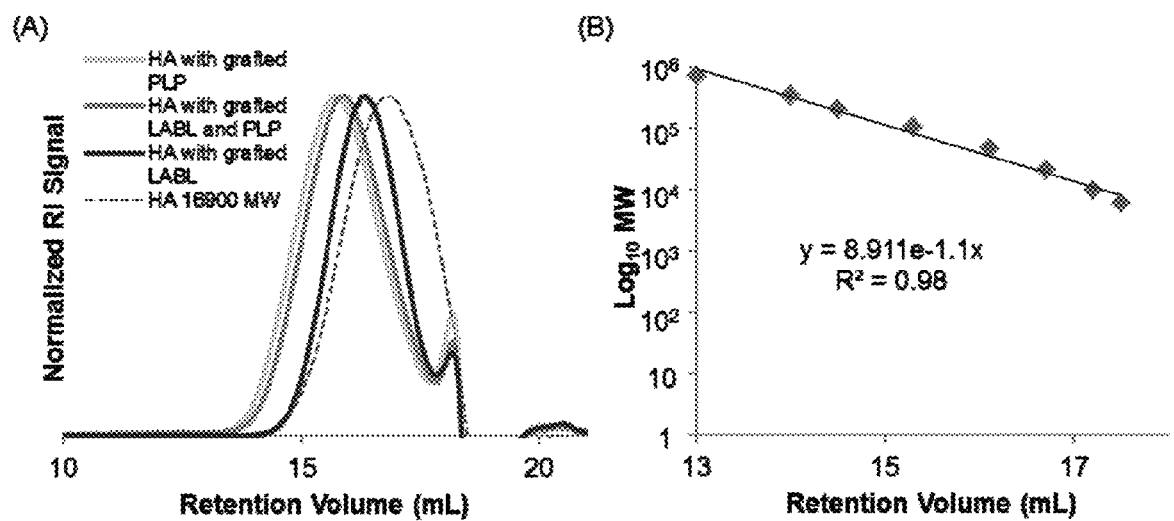

FIG. 7 shows (A) Size exclusion chromatography (SEC) analysis of Hyaluronic acid (HA) grafted with a single peptide Aminooxy-proteolipid peptide (PLP) or aminooxy-LABL peptide (LABL) or grafted with a 1:1 peptide mixture showed an increase in molecular weight (MW) as compared to unmodified HA. (B) Calibration curve for pullulan standards used to calculate HA polymer graft conjugate product MW.

Figure 8:
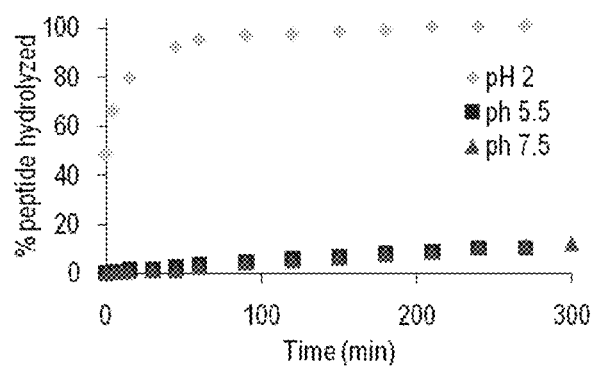

FIG. 8 is a graph depicting the release of Ao-LABL peptide from HA by hydrolysis of the N-oxime bond at three pH conditions. At pH 5.5 and 7.5, peptide concentration approaches 10% after ~240 minutes while 100% of the peptide is hydrolyzed from HA after 60 minutes at pH 2.

Figures 9A, 9B:
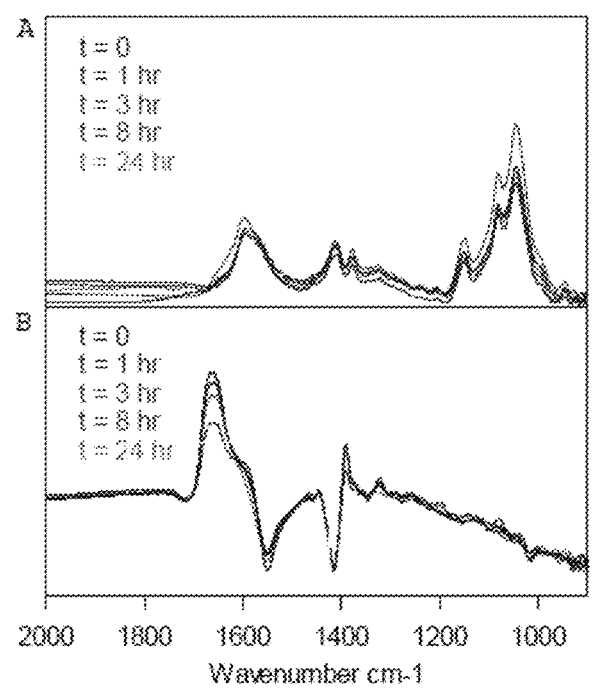

FIGS. 9A-9B are FTIR spectra of (A) a mixture of the poly acrylic acid (PAA) polymer (carboxylic acid side chains) with OCMH that showed no change in bonding environments and (B) the reaction of Poly N-Vinyl Formamide (PNVF) (amide acid side chains) with OCMH that showed a decrease in the amide peak at 1650 cm$^{-1}$ and an increase in the N-oxime bond peak as the appearance of a shoulder at 1600 cm$^{-1}$.

Figures 10A, 10B:
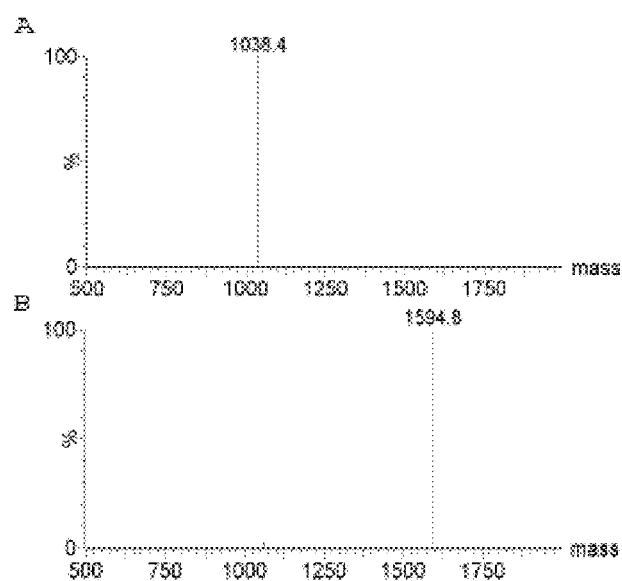

FIGS. 10A-10B are ESI+ mass spectroscopy of (A) purified Ao-LABL peptide with the expected mass of 1038 and (B) purified Ao-PLP peptide with the expected mass of 1594.

Figures 11A, 11B:
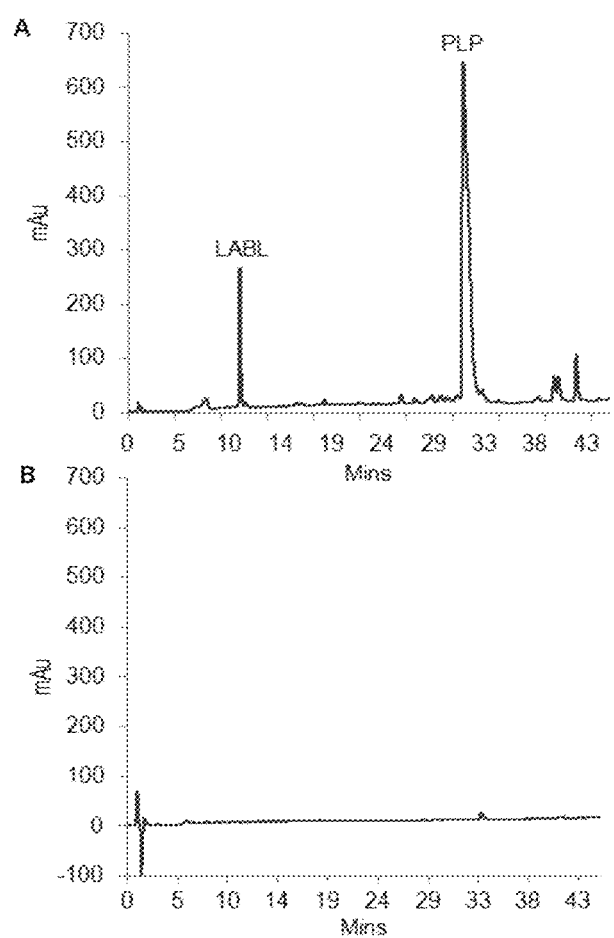

FIGS. 11A-11B are graphs depicting (A) an example high performance liquid chromatography (HPLC) chromatogram of peptides hydrolyzed from the conjugate product showing the presence of both the Ao-LABL and Ao-PLP peptides; and (B) HPLC chromatogram of dialysate showing the absence of both the AoLABL and Ao-PLP peptides suggesting nearly all peptide was reacted to HA.

Figure 12:
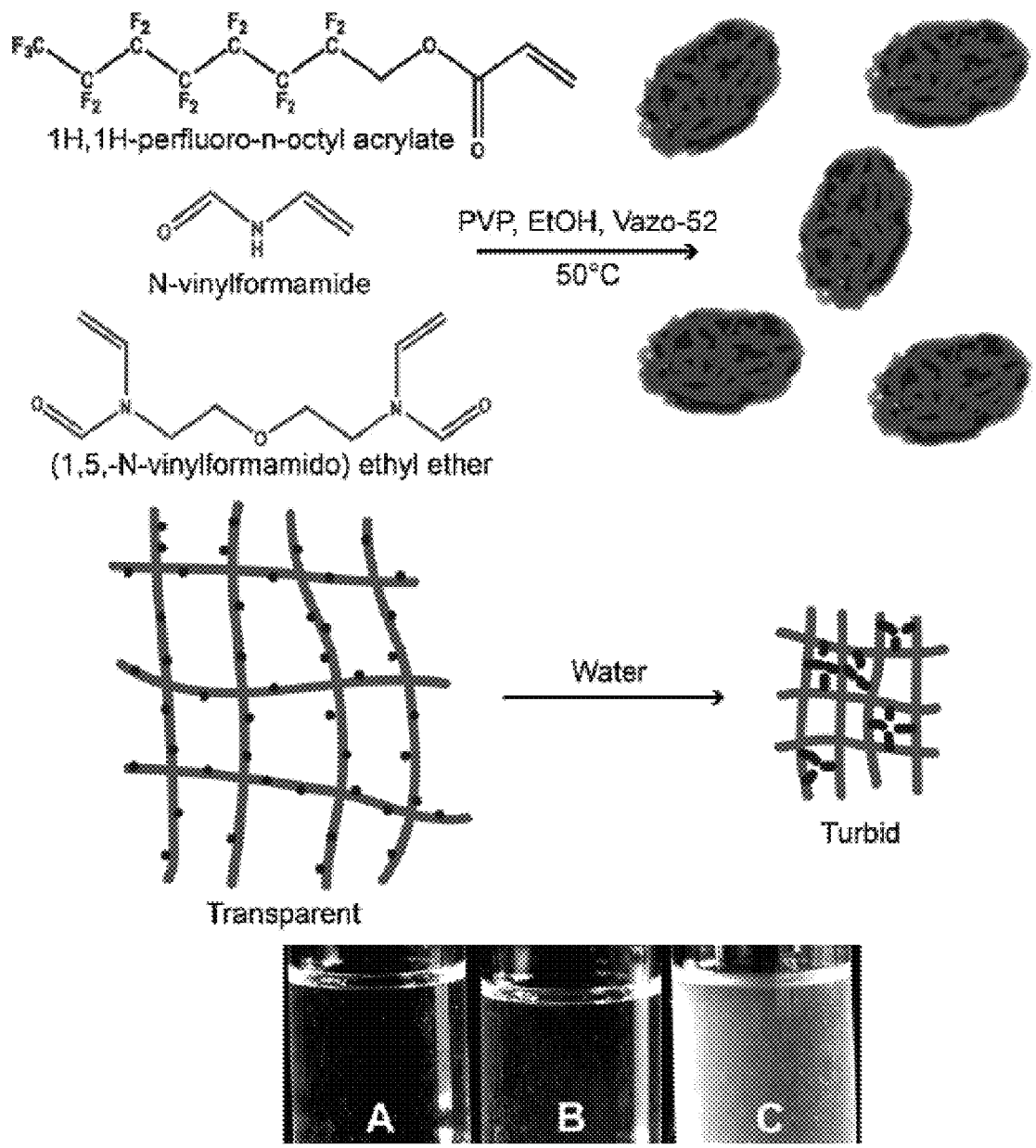

FIG. 12 depicts the nanoparticle (NP) synthesis in the top scheme. The middle scheme depicts the proposed interaction between fluorinated side chains as the product is transferred from ethanol to water and transitions from transparent to turbid. The photograph inset shows (A) reagent mixture prior to reaction, (B) product in ethanol after reaction, and (C) nanoparticle suspension in water after dialysis.

Figures 13A, 13B:
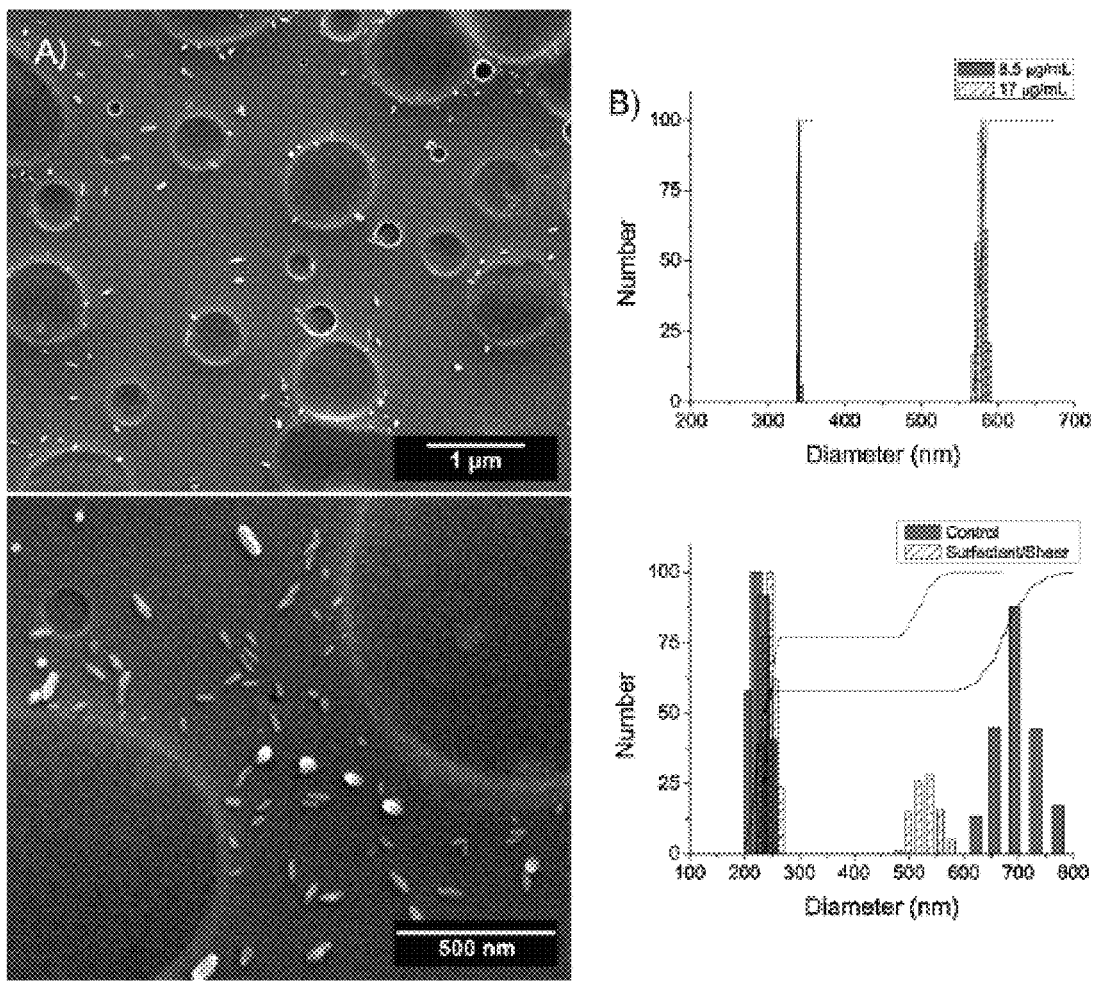

FIGS. 13A-13B depict (A) environmental scanning electron microscopy (ESEM) images of the fluorinated NPs, which appear as white spheres and ellipsoids. Image analysis using Image-Pro software revealed a mean particle size of 47.0±3.6 nm (95% confidence level). (B) dynamic light scattering (DLS) measurements of fluorinated NPs under different conditions; (top) size as a function of NP concentration (bottom) effect of Tween-20 and sonication on particle size. Under shear and in the presence of the surfactant, particle flocculation is reduced. The lines represent the cumulative distribution function.

Figures 14A, 14B, 14C:
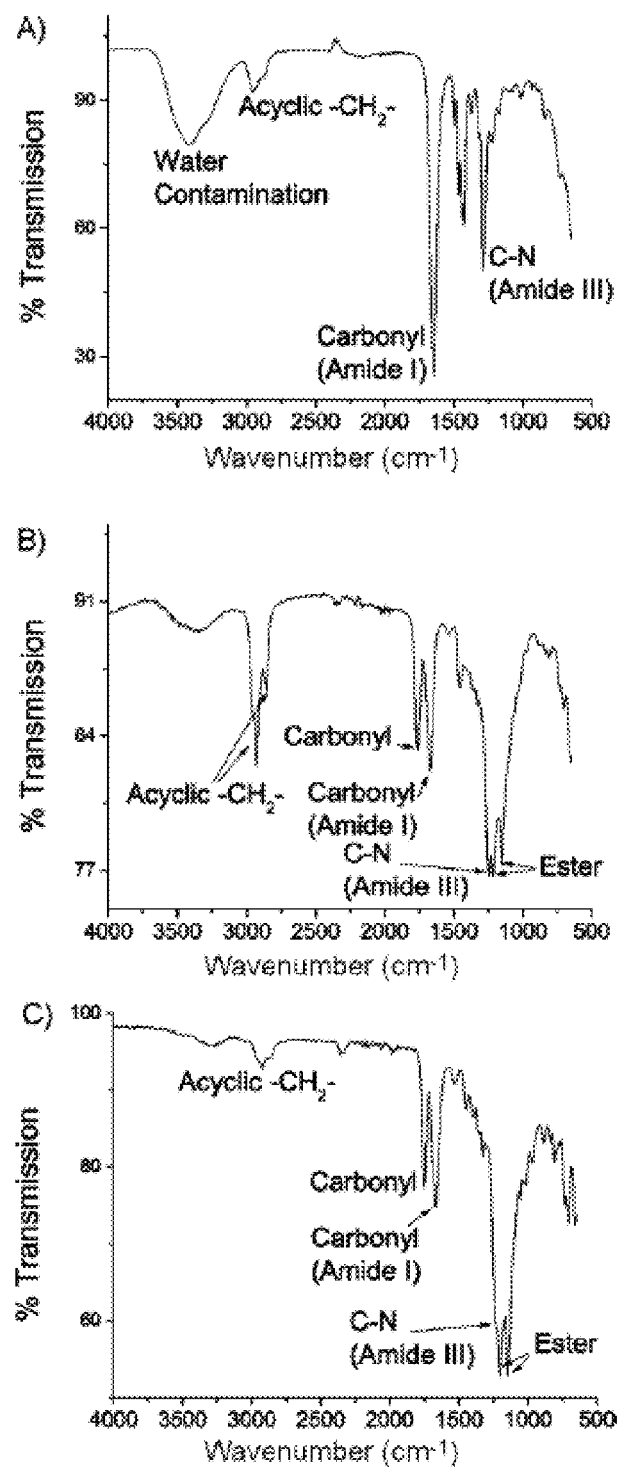

FIGS. 14A-14C depict FTIR spectrum of fluorinated NPs. The spectrum for (A) polyvinylpyrrolidone PVP is compared to (B) particles synthesized in the presence of PVP and (C) particles synthesized without PVP. Both spectra (B) and (C) show amide I and amide III peaks, suggesting that N-vinylformamide (NVF) is incorporated into the particles. Spectra (B) and (C) also show carbonyl peaks and ester peaks, suggesting the presence of the fluorinated ester acrylate group.

Figures 15A, 15B:
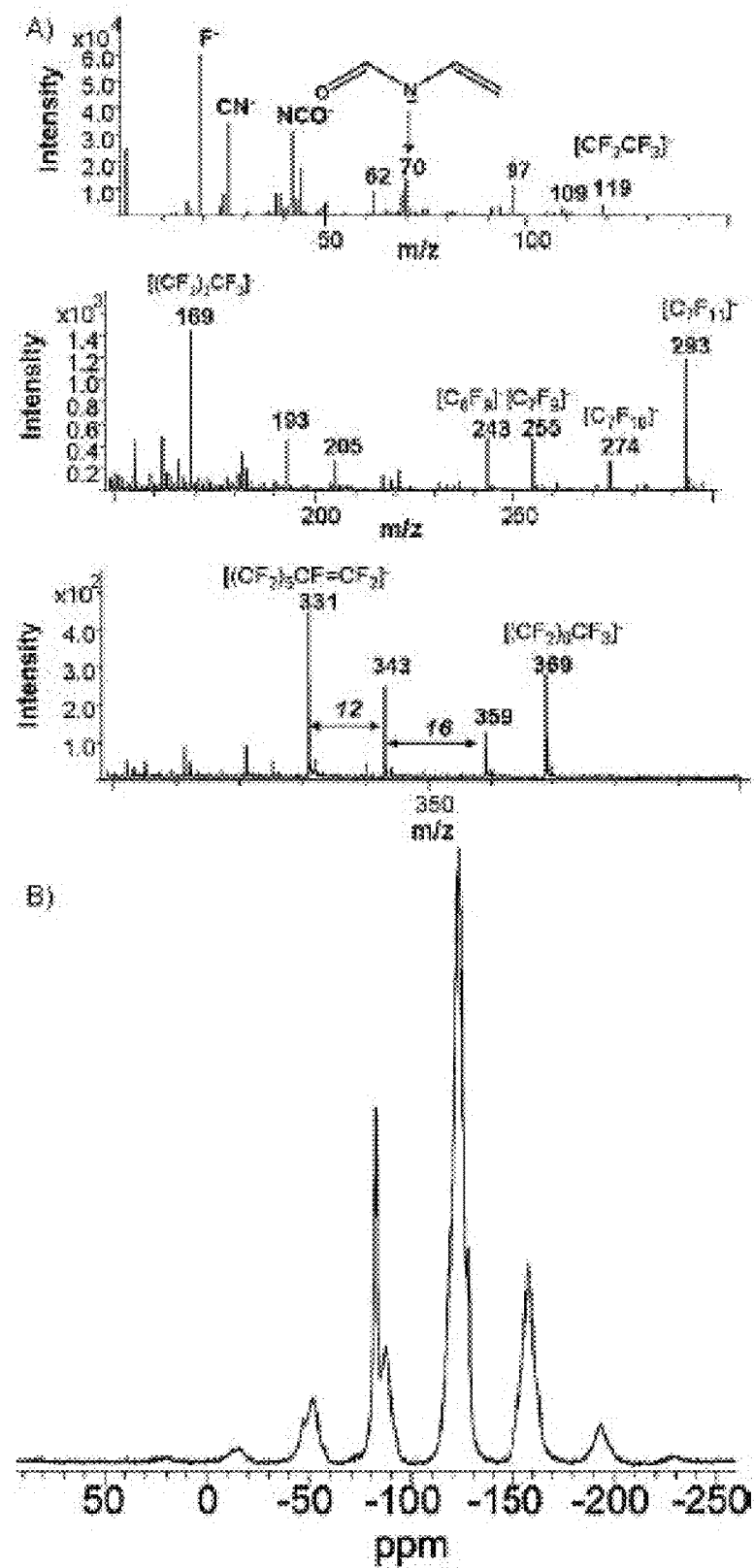

FIGS. 15A-15B depict (A) Negative secondary ion mass spectrometry (SIMS) images for NP samples suggest the presence of nitrogen-containing functional groups and fluorinated groups on the surface of the particles. (B) The solid state 19F NMR spectrum of the fluorinated NPs reveals peaks consistent with the presence of two different fluorine-containing sites in the fluorinated group. The peak at −82.1 ppm originates from $CF_3$ fluorine, and the one at −122.8 ppm from $CF_2$ fluorine. The $CF_2$ peak is surrounded by spinning sidebands.

Figure 16:
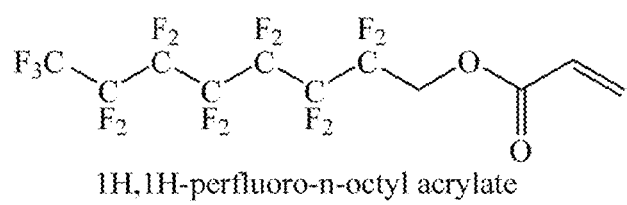
Figure 16:
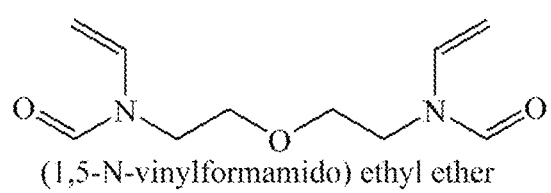
Figure 16:
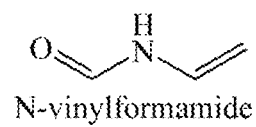
Figure 16:
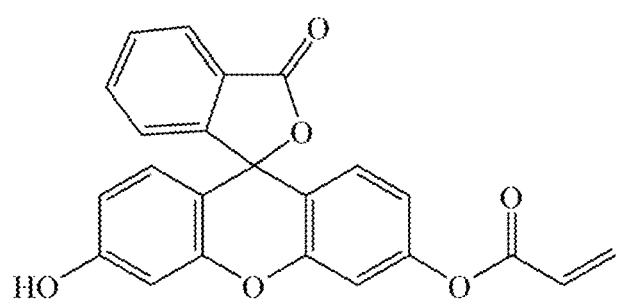
Figure 16:
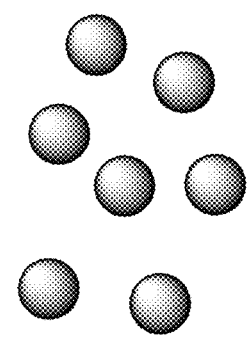

FIG. 16 depicts the synthesis of fluorinated-fluorescent NPs. For each batch, monomers were dissolved in ethanol containing PVP as a surfactant and Vazo-52 initiator. The reaction was carried out at 60° C. for 24 hours.

Figure 17A:
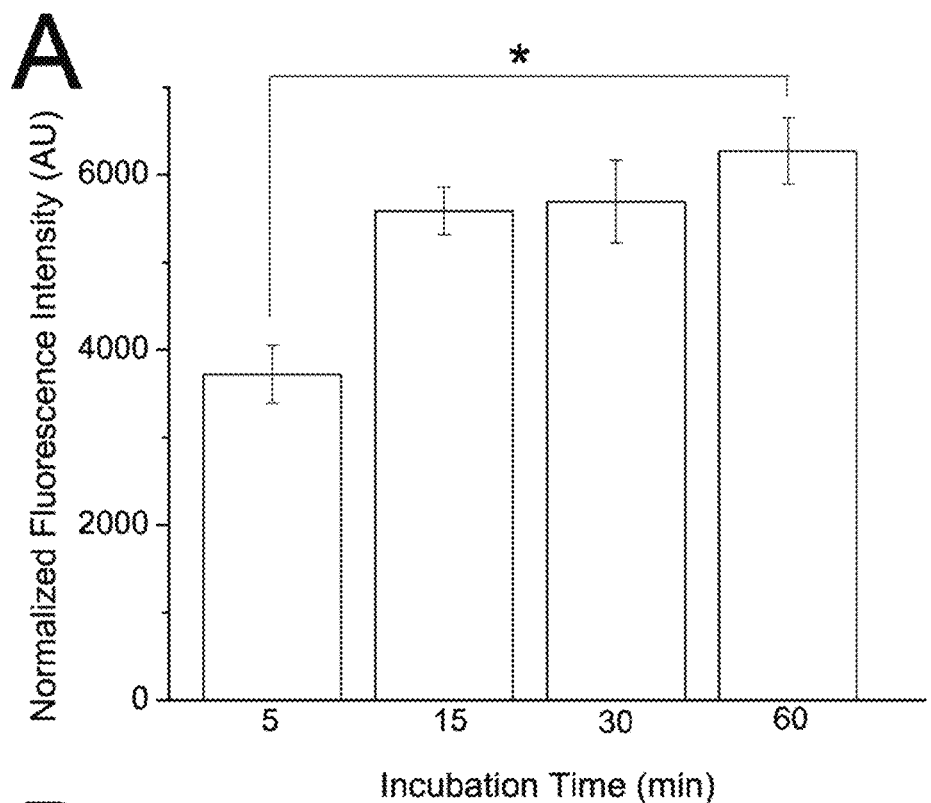
Figure 17B:
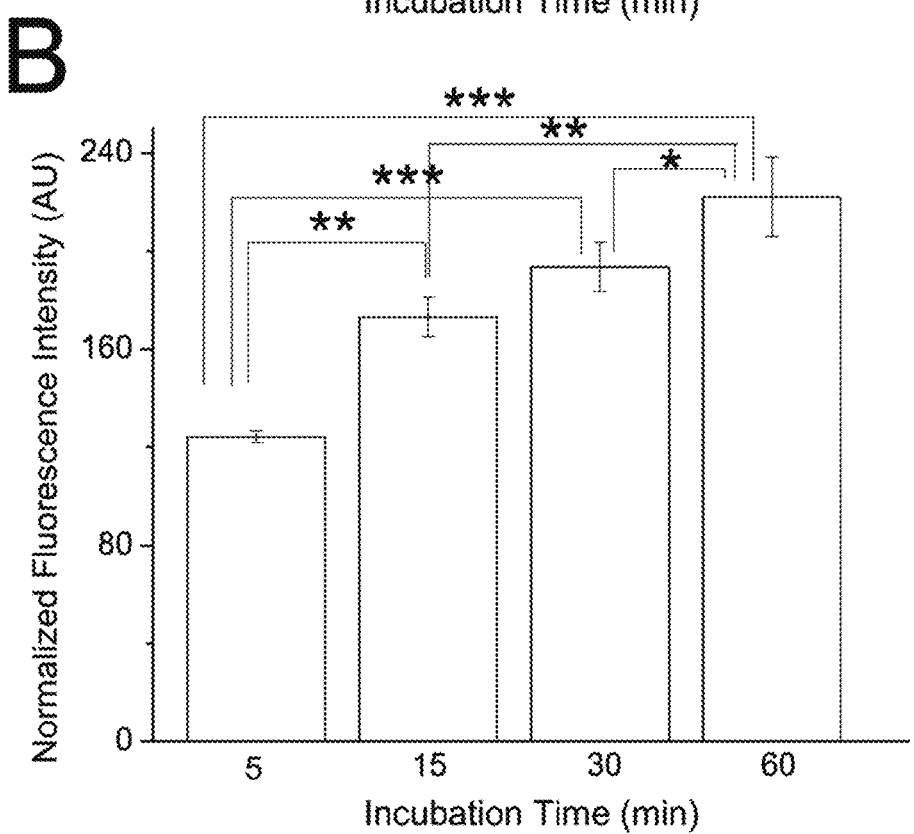

FIGS. 17A-17B depict normalized fluorescence intensity of LABL conjugated NPs (A) and non-conjugated NPs (B) in human umbilical vein endothelial cells (HUVECs). LABL was conjugated using Noxime chemistry. The results suggest a much greater normalized fluorescence intensity for the LABL-conjugated nanoparticles, most likely due to binding facilitated by the LABL peptide. Data are presented by mean±standard deviation. *$p<0.05$, $p<0.01$, and *$p<0.001$.

FIGS. 18A-18B are ESI+ mass spectroscopy of (A) NAG stock material and (B) the unpurified reaction product between NAG and Ao-peptide showing the product peak at ~1798 and product plus Na+ at 1821.

FIGS. 19A-19B are ESI+ mass spectroscopy of (A) NAG stock material and (B) the unpurified reaction product between NAG and Ao-peptide showing the product peak at ~1018 and product plus Na+ at ~1042.

Figure 20:
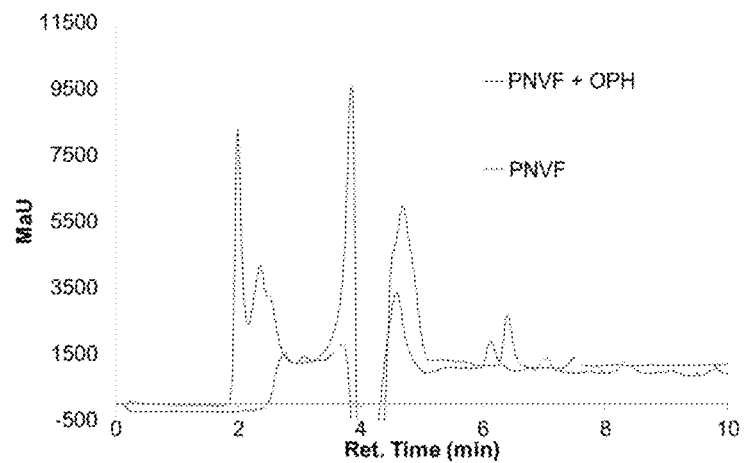

FIG. 20 shows HPLC chromatogram at 280 nm comparing Poly N-Vinyl Formamide (PNVF) starting material with PNVF reacted with O-Phenyl Hydroxylamine (OPH) in acetate buffer pH 5.5 for 24 hours. Shift in retention time to earlier time point indicates increase in hydrophobicity.

Figure 21:
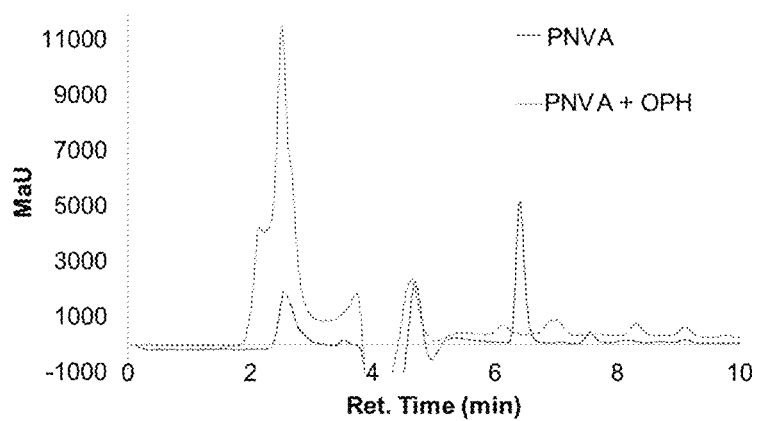

FIG. 21 shows HPLC chromatogram at 280 nm comparing Poly N-Vinyl acetamide (PNVFA) starting material with PNVFA reacted with OPH in acetate buffer pH 5.5 for 24 hours. Shift in retention time to earlier time point indicates increase in hydrophobicity.

Figure 22:
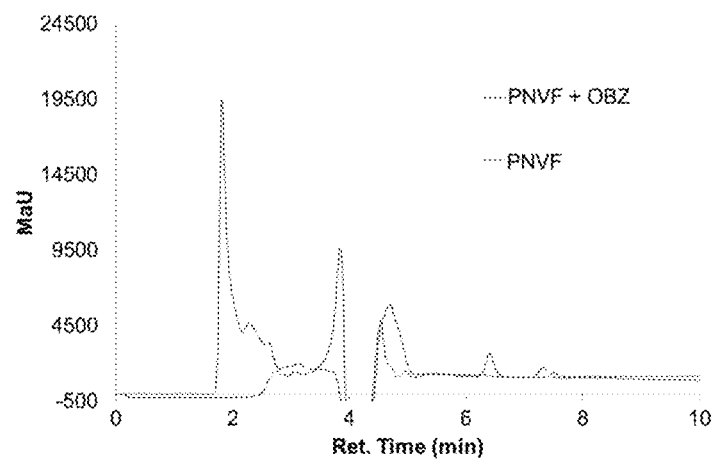

FIG. 22 shows HPLC chromatogram at 280 nm comparing PNVF starting material with PNVF reacted with OBZ in acetate buffer pH 5.5 for 24 hours. Shift in retention time to earlier time point indicates increase in hydrophobicity.

Figure 23:
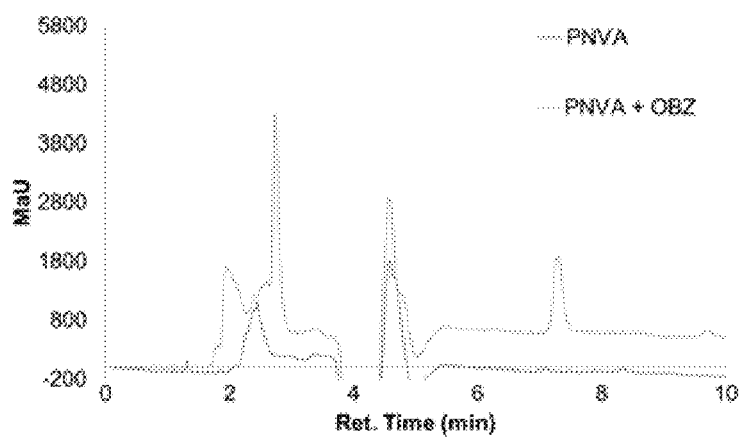

FIG. 23 shows HPLC chromatogram at 280 nm comparing PNVFA starting material with PNVFA reacted with OBZ in acetate buffer pH 5.5 for 24 hours. Shift in retention time to earlier time point indicates increase in hydrophobicity.

Figure 24:
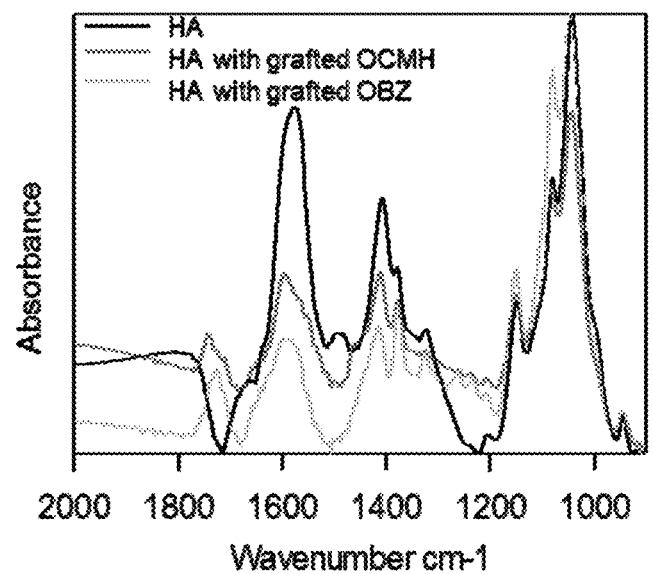

FIG. 24 shows the FTIR spectra of graft polymer products showing new peaks at ~1750 and ~1250 cm$^{-1}$ and loss of the peak at ~1500 cm−1 when compared to the HA spectra.

The patent or application file contains at least one drawing executed in color. Copies of this patent or patent application publication with color drawing(s) will be provided by the Office upon request and payment of the necessary fee.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure relates generally to conjugate compositions comprising an N-oxime bond and associated methods. More particularly, the present disclosure relates to conjugate compositions wherein a compound comprising at least one reactive amide group is reacted with a compound comprising at least one reactive aminooxy group to form a conjugate composition comprising at least one N-oxime bond.

In one embodiment, the present disclosure provides a method of making a conjugate comprising: providing a compound comprising at least one reactive amide group; providing a compound comprising at least one reactive aminooxy group; and reacting the compound comprising at least one reactive amide group with the compound comprising at least one reactive aminooxy group to form a conjugate composition comprising at least one N-oxime bond. Specific examples of suitable compounds comprising a reactive amide group or a reactive aminooxy group will be discussed in more detail below.

In one embodiment, a method of making a conjugate of the present disclosure may be represented as follows:

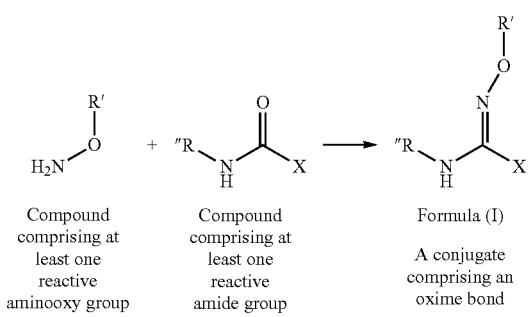

| Compound comprising at least one reactive aminooxy group | Compound comprising at least one reactive amide group | Formula (I) A conjugate comprising an oxime bond | wherein R' or R" may be independently selected to be any of a number of compounds including a peptide, a protein, a polymer, a saccharide, a polysaccharide, nucleic acid, a small molecule, etc. and wherein X may be H, $C_nH_{(n+2)}$ or other atoms. In another embodiment, the conjugate may be a reduced form of Formula I represented by the following Formula (II):

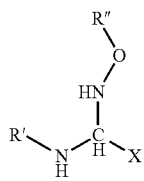

wherein R' is derived from a compound comprising at least one reactive amide group, R" is derived from a compound comprising at least one reactive aminooxy group, and X is H, $C_nH_{(n+2)}$ or other atoms.

The present disclosure is based, at least in part, on the discovery that N-oxime chemistry provides an opportunity to conjugate a compound comprising a reactive amide group with a compound comprising a reactive aminooxy group in a specific manner due to the increased reactivity of the amino ester bond for an amide group. Previously, it was believed that mainly aldehyde and ketone groups were reactive with aminooxy groups. However the presence of aldehydes or ketones often results in highly hydrophobic molecules or polymers which is undesirable. (Gajewiak 2006, Heredia 2007, Hwang 2007). While not being bound by any particular theory, it is currently believed that the presence of the reactive aminooxy group on a compound may allow for complete de-protection of the compound prior to synthesis of a conjugate. For example, reactive amides would selectively react with aminooxy groups over primary amines. Additional details regarding oxime chemistry, which may be applied in whole or in part using Noxime chemistry, may also be found in U.S. Patent Publication 2010/0047225, the relevant portions of which are herein incorporated by reference.

One of the many advantages of the present disclosure, many of which are not discussed herein, is that N-oxime chemistry can be carried out in aqueous solvents and avoids many of the harsh catalysts or reaction conditions currently used to create conjugated compounds. Additionally, the reaction can be conducted at lowered temperatures and the reaction efficiency becomes dependent on reactant solubility providing a highly scalable process to manufacture conjugates. In some embodiments, the reaction may be carried out in buffered aqueous media, at pH conditions of 4-8, and decreased temperatures, such as about 20-30° C., although a broader range of temperatures and solvents may also be suitable. In some embodiments, the methods of the present disclosure may allow an increased product yield, reduced purification steps, and greater product stability. Accordingly, in some embodiments, the reaction of a compound comprising at least one reactive amide group with a compound comprising at least one reactive aminooxy group may occur under any suitable conditions known to those of skill in the art, including conditions wherein a catalyst is not present.

As previously mentioned, a conjugate of the present disclosure may be made by reacting a compound comprising at least one reactive amide group with a compound comprising at least one reactive aminooxy group. Any compound comprising a reactive amide group may be suitable for use in the present disclosure. As used herein, the term "reactive amide group" refers to an amide group that is capable of reacting with a reactive aminooxy group to form an N-oxime bond. Examples of suitable compounds for use in the conjugates of the present disclosure include, but are not limited to, polymers comprising a reactive amide group, monomers comprising a reactive amide group, proteins comprising a reactive amide group, peptides comprising a reactive amide group, saccharides comprising a reactive amide group, polysaccharides comprising a reactive amide group, nucleic acids comprising a reactive amide group (DNA, RNA, etc.) and small molecules comprising a reactive amide group. The reactive amide group may be located anywhere on the compound provided it is still capable of reacting with a reactive aminooxy group. For example, a reactive amide group may be present in a side-chain, an end-group, or connected to the compound through one or more linkers. As will be recognized by one of ordinary skill in the art with the benefit of this disclosure, synthesis of a compound comprising a reactive amide group may be accomplished by functionalizing a desired compound with an amide group through procedures well known to those of skill in the art.

In some specific embodiments, a compound comprising a reactive amide group may include polymers such as HA, PNVF, an amide functionalized poly(ethylene glycol) derivative, chondroitin sulfate, dermatan sulfate and poly(ethylene glycol) derivative functionalized with one or more amides. In some specific embodiments, a compound comprising a reactive amide group may include small molecules such as NVF or derivatives thereof, acetaminophen, formoterol, and those disclosed in U.S. Patent Publication Nos. 2008/0103091 and 2005/0107585 and U.S. Pat. Nos. 5,863,889 and 6,075,004, the relevant portions of which are hereby incorporated by reference in their entirety. In some specific embodiments, a compound comprising a reactive amide group may include carbohydrates such as NAG. In some specific embodiments, a compound comprising a reactive amide group may include 6'-sialyl-N-acetyllactosamine sodium salt, 3'-N-acetylneuraminyl-N-acetyllactosamine sodium salt, 3'-sialyllactose, 6'-sialyllactose sodium salt, acetylcarnosine, N-acetylated blood group antigens, cytidine-5'-monophospho-N-acetylneuraminic acid sodium salt, 1,2-diformylhydrazine, di-(N-acetyl)chitobiose, colchicine, linezolid, 2-propenyl-N-acetyl-neuramic acid, orlistat, sulfacetamide, erbstatin, N-acylsphingosine, lewis-Y hexasaccharide, lewis-B tetrasaccharide, lewis-Y tetrasaccharide, leupeptin, melatonin, N-formyl-L-sarcolysin, NSC334340, N-formylmethionyl-leucyl-tyrosine, N-Linked high mannose glycans, and S-nitroso-N-acetylpenicillamine. Similarly, compounds such as fluorophores, fluorinated compounds, radioactive compounds, X-ray contrast agents, etc. may also be used in the conjugates of the present disclosure. This list is by no means exhaustive as there are potentially thousands of compounds comprising a reactive amide group. One of ordinary skill in the art with the benefit of this disclosure would be able to select an appropriate compound comprising a reactive amide group to be used in the conjugate compositions of the present disclosure based on, inter alia, the manner in which the conjugate would be used.

Similarly, any compound comprising a reactive aminooxy group may be suitable for use in the present disclosure. As used herein, the term "reactive aminooxy group" refers to an aminooxy group that is capable of reacting with a reactive amide group to form an N-oxime bond. Examples of suitable compounds for use in the present disclosure include, but are not limited to, polymers comprising a reactive aminooxy group, monomers comprising a reactive aminooxy group, proteins comprising a reactive aminooxy group, peptides comprising a reactive aminooxy group, polysaccharides comprising a reactive aminooxy group, nucleic acids comprising a reactive aminooxy group (DNA, RNA, etc.) and small molecules comprising a reactive aminooxy group. The reactive aminooxy group may be located anywhere on the compound provided it is still capable of reacting with a reactive amide group. For example, the reactive aminooxy group may be present in a side-chain, an end-group, or connected to the compound through one or more linkers. As will be recognized by one of ordinary skill in the art with the benefit of this disclosure, synthesis of a compound comprising a reactive aminooxy group may be accomplished by functionalizing a desired compound with an aminooxy group through procedures well known to those of skill in the art.

In some specific embodiments, a compound comprising a reactive aminooxy group may include an O-Allylhydroxylamine or polymers thereof, an aminooxy functionalized poly(ethylene glycol) derivative, and poly(ethylene glycol) derivative functionalized with multiple aminooxy groups. In some specific embodiments, a compound comprising a reactive aminooxy group may include small molecules such as OCMH hemihydrochloride, and those disclosed in U.S. Patent Publication Nos. 2008/0103091 and 2005/0107585 and U.S. Pat. Nos. 5,863,889 and 6,075,004, the relevant portions of which are hereby incorporated by reference in their entirety. In some specific embodiments, a compound comprising a reactive aminooxy group may include CID 19862450, CID 21734323, CID 21873114, CID 21941113, CID 22184284, CID 11528351, CID 3306142 and canaline. Similarly, compounds such as fluorophores, fluorinated compounds, radioactive compounds, X-ray contrast agents, etc. may also be used in the conjugates of the present disclosure. This list is by no means exhaustive as there are potentially thousands of compounds comprising a reactive aminooxy group. One of ordinary skill in the art with the benefit of this disclosure would be able to select an appropriate compound comprising a reactive aminooxy group to be used in the conjugate compositions of the present disclosure based on, inter alia, the manner in which the conjugate would be used.

In some embodiments, a compound comprising at least two reactive amide groups may be reacted with a compound comprising at least two reactive aminooxy groups to form a crosslinked conjugate comprising at least two N-oxime bonds. Again, the reactive aminooxy groups and the reactive amide groups may be located anywhere on the compounds provided that the compounds are still capable of reacting with one another to form a crosslinked conjugate. For example, the reactive aminooxy group or reactive amide groups may be present in a side-chain, an end-group, or connected to the compound through one or more linkers. As will be recognized by one of ordinary skill in the art with the benefit of this disclosure, synthesis of compounds comprising at least two reactive aminooxy groups and compounds comprising at least two reactive amide groups may be accomplished by functionalizing a desired compound with an aminooxy group or amide group, respectively, through procedures well known to those of skill in the art. In some specific embodiments, suitable crosslinkers for forming a crosslinked conjugate of the present disclosure may be represented as follows:

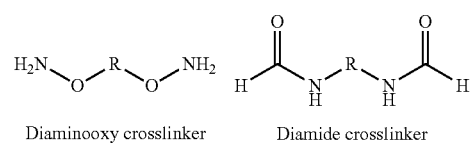

Diaminooxy crosslinker       Diamide crosslinker wherein R may be independently selected to be any of a number of compounds including a peptide, a protein, a polymer, a saccharide, a polysaccharide, nucleic acid, a small molecule, etc. In some specific embodiments, a suitable crosslinker may include a diaminooxy poly(ethylene glycol), a diamide poly(ethylene glycol), N,N,N',N'-tetraacetylethylenediamine, etc. In some embodiments, a suitable crosslinker may be "dendritic," owing to the presence of successive branch points. As would be recognized by a person of ordinary skill in the art with the benefit of this disclosure, the crosslinked conjugates of the present disclosure will comprise at least two N-oxime bonds, but may comprise any number of N-oxime bonds in excess of one, such as two, three, four, five, six, etc.

A conjugate of the present disclosure may be useful in a multitude of applications. As would be recognized by a person of ordinary skill in the art with the benefit of this disclosure, the methods and conjugate compositions of the present disclosure may be utilized in any application where it is desirable to conjugate one compound with another. In some specific embodiments, the methods and compositions of the present disclosure may be used in detection or diagnostic applications, microarrays or other assay schemes, protein modification (e.g. PEGylation, glycosylation, etc.), as a linker, in the production of colloids or other materials, production of therapeutics, etc. In some embodiments, the conjugates of the present disclosure may be included in a pharmaceutically acceptable form, for example in a pharmaceutically acceptable carrier, for administration to a subject.

To facilitate a better understanding of the present disclosure, the following examples of certain aspects of some embodiments are given. In no way should the following examples be read to limit, or define, the entire scope of the invention.

EXAMPLE 1

Materials

NAG, GLU, NVF, research grade sodium acetate, acetic acid, OCMH hemihydrochloride, and D2O were purchased from Sigma. HA, with an average MW of 31 kD was purchased from Lifecore. Amino acids were purchased from Peptides International. Analytical grade acetonitrile and synthesis grade trifluoro acetic acid (TFA) were purchased from Fisher Scientific. Peptides and PNVF were synthesized by the laboratory. Water was provided by a Labconco Water PRO PS ultrapure water purification unit.

Methods

Peptide Synthesis.

Aminooxy peptides were synthesized using 9-fluorenylmethyloxycarbonyl-protected amino acid chemistry on polyethylene glycol-polystyrene resins. The peptides synthesized were aminooxy-LABL (aminooxy-ITDGEATDSG, Ao-LABL), a cell adhesion molecule antagonist, and aminooxy-proteolipid peptide (PLP) (aminooxy-HSLGKWLGHPDKF, Ao-PLP), a known antigen epitope in multiple sclerosis. Peptides were deprotected, cleaved from resin, and isolated by precipitation in ether. Purification was completed using preparatory HPLC followed by lyophilization. Peptide purity was assessed using analytical HPLC and the identity of the synthesized peptide was confirmed by electrospray ionization mass spectrometry.

Reaction of Aminooxy Molecules to Monomer/Polymer.

The reaction conditions were identical for all monomers and polymers used (NAG, GLU, PNVF and HA). The aminooxy-containing small molecule OCMH and peptide species were both tested. Polymers were first dissolved into 20 mM acetate buffered saline (pH 5.5±0.1). Once dissolved, OCMH or aminooxy-peptide was added to the solution. When more than one peptide species was added, both were weighed out separately then added simultaneously. After addition of the aminooxy species, the reaction solution pH was adjusted back to pH 5.5±0.1. For kinetic experiments, samples were taken from the reaction vessel at predetermined time points and analyzed immediately. For peptide conjugates the reaction products were purified by dialysis to remove excess free peptide, and lyophilized. Exact procedure for reaction can be found in supplemental materials.

Mass Spectroscopy.

Masses of conjugates and of synthesized peptides were determined by electrospray ionization mass spectroscopy by using a waters LCT premier ESI mass spectrometer running MassLynx software.

Fourier Transform Infrared Spectroscopy.

Changes in bonding environments during reaction were monitored using a Bruker Tensor 27 FTIR spectrometer equipped with a ZnSe attenuated total reflectance (ATR) plate (Pike Technologies). FTIR spectra were collected at room temperature (25° C.). Data were collected over 256 composite scans with a resolution of 4 $cm^{-1}$. The samples were analyzed in 20 mM acetate buffered saline at a concentration of 3 mg/mL. Spectra from OCMH in solution were subtracted using the OPUS spectroscopy software and data were further analyzed using GRAMS/AI (Galactic, Inc.).

Nuclear Magnetic Resonance Spectroscopy.

For structural analysis of the various monomers and conjugates, samples were dissolved in $D_2O$ to a concentration of 10 mg/mL. H1 and C13 spectra were acquired on a Bruker 400 MHz spectrometer at 25° C.

Gel Permeation Chromatography.

The change in molecular weight of HA conjugates was determined using a Viscotek GPC max VE 2001 GPC solvent/sample module, VE 3580 refractive index detector, and 270 Dual Detector with right angle light scattering. Samples were separated by utilizing a tandem column setup of two Viscogel, GMPW×1 grade, columns (Viscotek) at a flow rate of 1 ml/min and isocratic elution in water for 30 min.

High Performance Liquid Chromatography.

Peptide was quantified by gradient reversed-phase HPLC (SHIMADZU) using a Vydac HPLC protein and peptide C18 column. The HPLC consisted of a SCL-20A SHIMADZU system controller, LC-10AT VP SHIMADZU liquid chromatograph, SIL-10A XL SHIMADZU auto-injector set at 75 µL injection volume, DGU-14A SHIMADZU degasser, sample cooler, and SPD-10A SHIMADZU UV-vis detector (220 nm). The HPLC-UV system was controlled by a personal computer equipped with SHIMADZU class VP Software. Gradient elution was carried out at constant flow of 1 mL/min, from 100% A to 35% A (corresponding to 0% B to 65% B) for 50 min, followed by an isocratic elution at 75% B for 3 min. Mobile phase compositions were (A) acetonitrile-water (5:95) with 0.1% TFA and (B) acetonitrile-water 90:10, v/v) with 0.1% TFA. At the end of each analysis, the cartridge was re-equilibrated at initial conditions at 1 mL/min flow rate for 5 min with A.

Discussion

Figure 1:
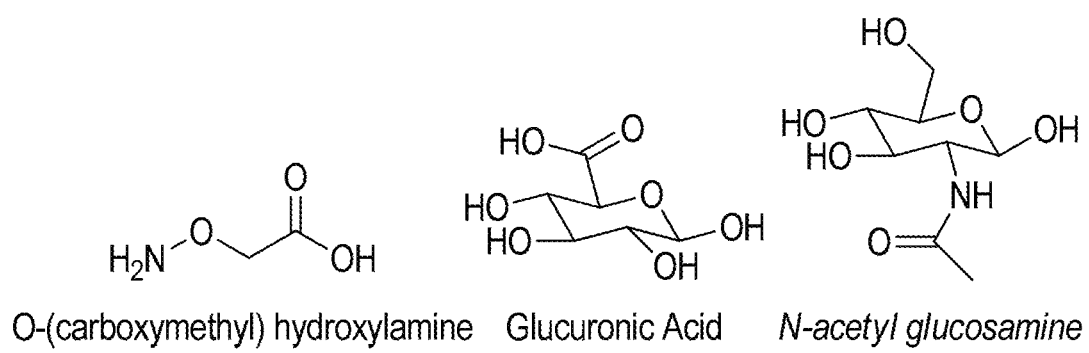
FIG. 1 depicts structures of O-(carboxymethyl)hydroxylamine (OCMH), glucuronic acid (GLU), and N-acetyl glucosamine (NAG).
Figures 2A, 2B:
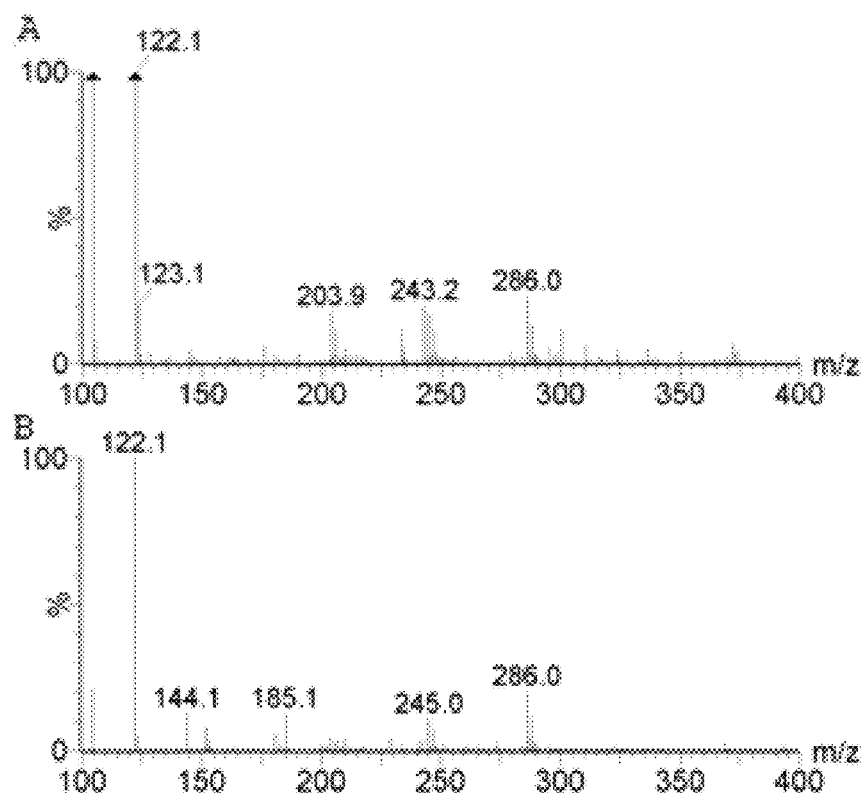
FIGS. 2A-2B are electro spray ionization (ESI)+mass spectroscopy of (A) GLU stock material and (B) the unpurified mixture of GLU and OCMH showing the absence of any product peak.
Figures 3A, 3B:
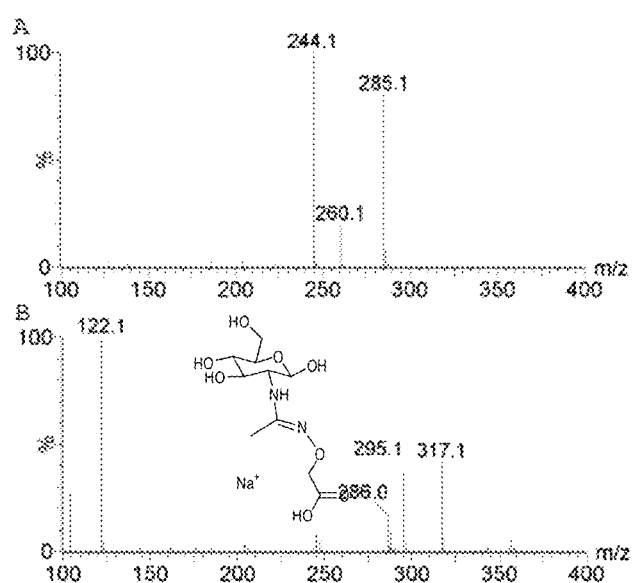
FIGS. 3A-3B are ESI+ mass spectroscopy of (A) NAG stock material and (B) the unpurified reaction product between NAG and OCMH showing the product peak at 295 and product plus Na+ at 317.

Using OCMH, the potential for an aminooxy reaction to the monomers of HA, GLU and NAG, was probed. Both of these groups display a carbonyl carbon; a carboxylic acid on GLU and an amide on NAG (FIG. 1). Individual monomers were reacted with OCMH in an acetate buffered saline and the product was analyzed by mass spectroscopy. The spectrum for the reaction product between GLU and OCMH (FIG. 2) showed the presence of the GLU (MW=144.1) and OCMH (MW=91), however, no reaction product was present. In the mass spectra for the reaction between NAG and OCMH, a peak at a mass of 317 Da was found in addition to the reactants themselves (FIG. 3). This molecular mass was equivalent to the theoretical mass expected for aminooxy conjugation through the N-acetyl site of NAG, thus supporting the possibility of an N-oxime reaction scheme. It should be noted that in both mass spectra for GLU and NAG, there is a peak at 286 for GLU and at 285 for NAG in the stock material that also appears in the final product.

Figure 4:
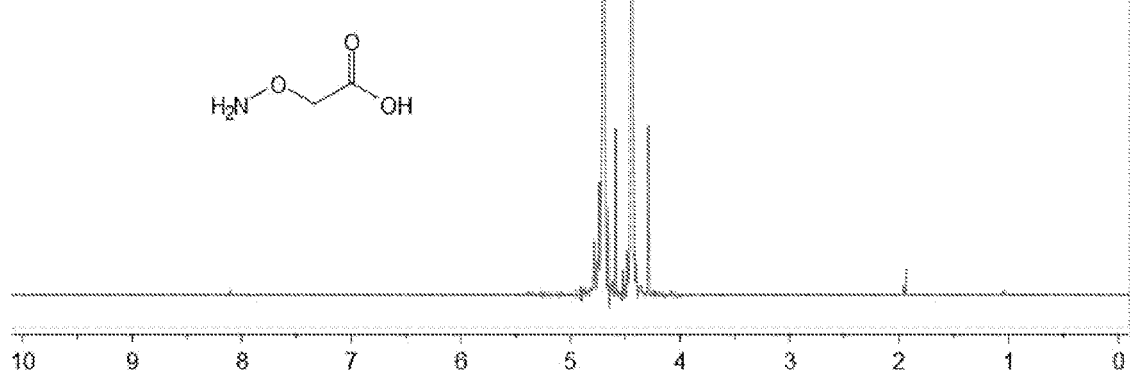
FIGS. 4A-4C are $^1$H Nuclear magnetic resonance (NMR) spectra for (A) OCMH, (B) NAG and (C) oxime product of OCMH+NAG. The OCMH and O-benzyl hydroxylamine (OBZ) spectra show the appearance of new peaks suggesting oxime bond formation at a—5.0 ppm, b—~6.7 and 7.2 ppm.
Figure 4:
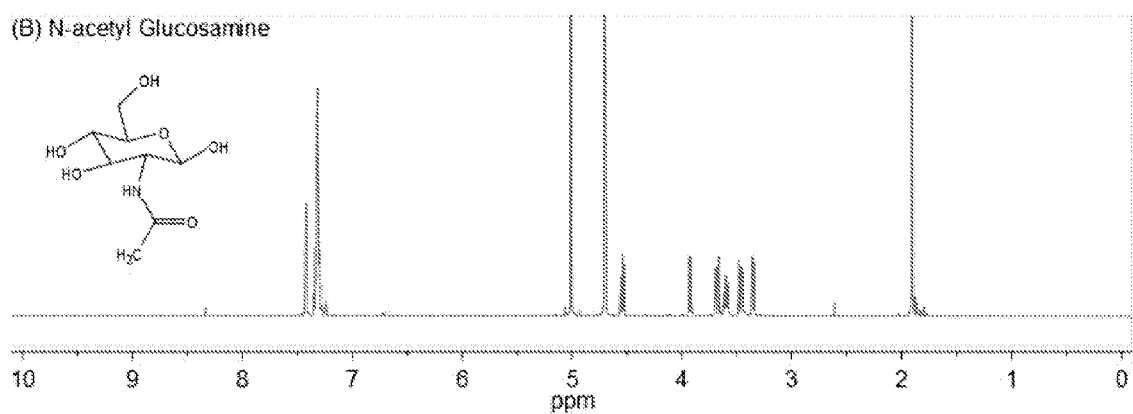
Figure 4:
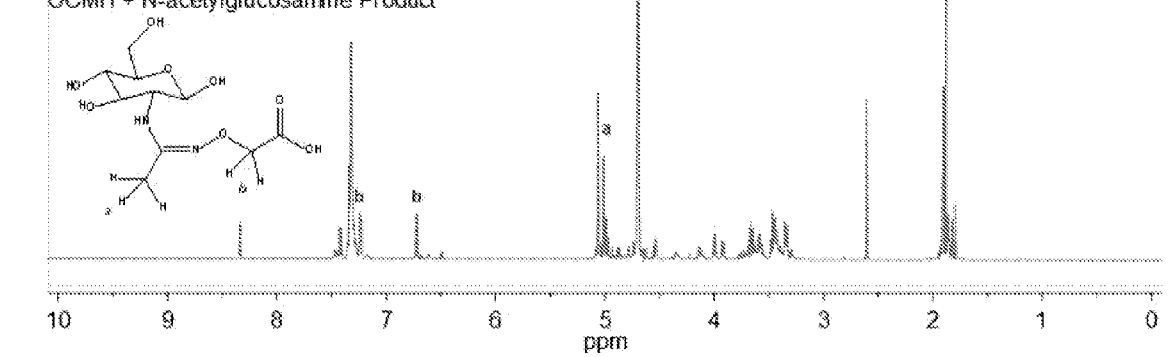
Figure 5A:
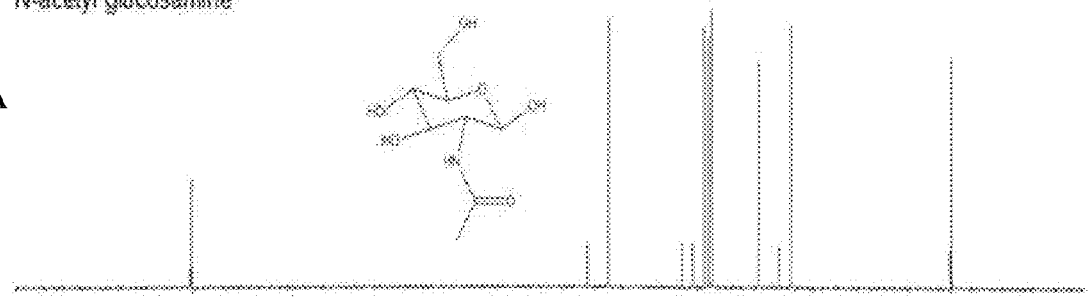
FIGS. 5A-5C are C13 NMR spectra that showed expected changes from (A) NAG monomer and (B) OCMH to (C) reaction product of NAG monomer and OCMH. The product spectra showed that the amide carbon peak (~175 ppm) shifted to ~150 ppm indicative of the N-oxime bonding environment.
Figure 5B:
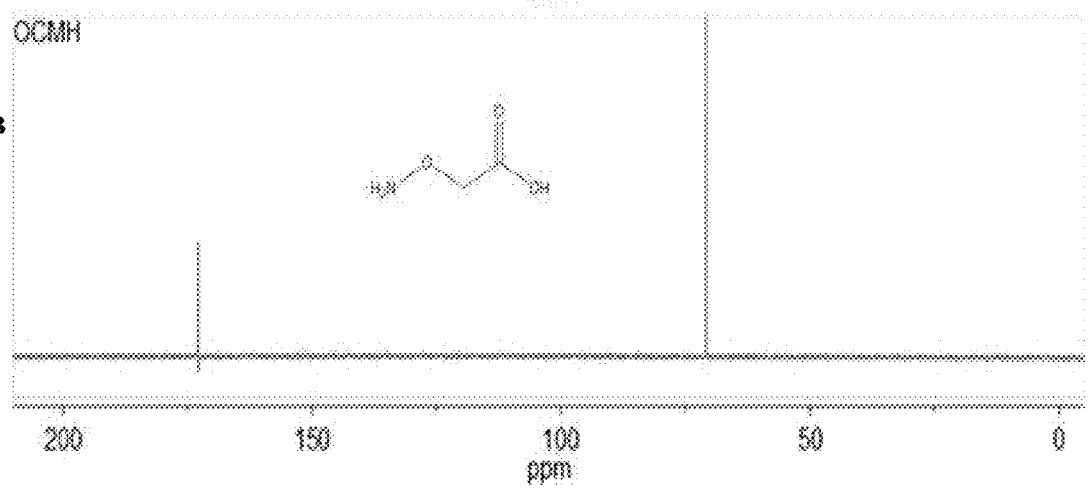
Figure 5C:
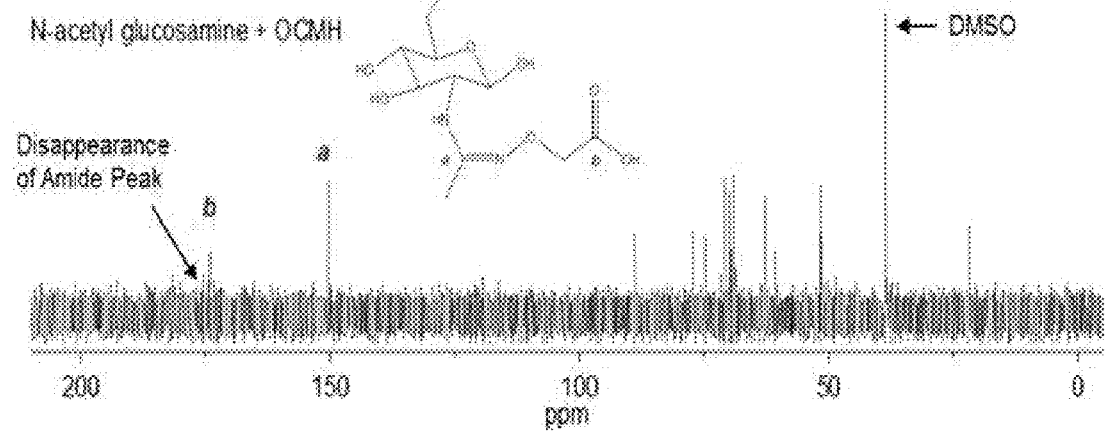

With the mass spectroscopy data suggesting a reaction was occurring, the products were analyzed to identify the groups involved in the reaction process. The NAG+OCMH product was analyzed by H1 (FIG. 4) and C13 (FIG. 5) NMR. The H1 NMR data showed the appearance of new environments at ~2 ppm as a result of the methyl hydrogens in the OCMH backbone, and at 6.5 and 7.5 ppm due to the appearance of the N-oxime bonding environments. The ring environment from 3-4 ppm shifted slightly, which could be due to interactions between NAG and the new OCMH side chain groups. C13 NMR was used to identify the effected carbons in the reaction. The amide environment was indeed involved in the reaction as the amide carbon (~175 ppm) shifts to 150 ppm, indicative of an N-oxime-bonded carbon. Additionally, the carboxylic acid environment of unreacted OCMH appeared in the product spectra at 180 ppm along with the methyl carbons in the backbone of OCMH at 25 ppm. The NMR data supported the notion that the N-acetyl amide groups do confer aminooxy reactivity.

In addition to the NMR data, changes in bonding environments of the reactants were monitored throughout the course of the reaction. The experiment was conducted with the aminooxy-reactive molecule OCMH in 10-fold excess and any changes in either GLU or NAG were monitored using FTIR over a 24 hour reaction period. For all FTIR spectra, the free OCMH in solution was subtracted resulting in the FTIR spectra showing only changes in NAG or GLU. When the reaction between GLU and OCMH was analyzed, the FTIR data showed no change in the bonding environment over the entire 24 hr period (FIG. 6A). When the reaction of NAG+OCMH was analyzed (FIG. 6B), the amide bonding environments at 1650 and 1550 cm$^{-1}$ decreased throughout the course of the reaction. In addition to the disappearance of the amide bonding environments, two new bonding environments appeared; the carboxylic acid environment due to the addition of OCMH to NAG at 1700 cm$^{-1}$ and the N-oxime environment at 1250 cm$^{-1}$. Thus, mass spectroscopy, NMR, and FTIR data demonstrated that a reaction is occurring between the amide carbon of NAG and the aminooxy of OCMH.

An additional control was conducted to further evaluate aminooxy reactivity to free amides. In this study, PAA (only carboxylic acid side chains) and PNVF (only N-formyl side chains) were probed for aminooxy reactivity. PAA exhibited no reactivity as expected (FIG. 9A) while PNVF reacted with OCMH. A time course analysis using FTIR showed a decrease in amide peak at 1650 cm$^{-1}$ and an increase in N-oxime bond peak as the appearance of a shoulder at 1600 cm$^-$ (FIG. 9B).

N-oxime chemistry was further probed by grafting an aminooxy reactive peptide to HA. The peptides LABL and PLP were synthesized with a terminal aminooxy group to confer reactivity. The peptide molecular weights were confirmed by mass spectroscopy (FIG. 10A and FIG. 10B) with a purity >90% as determined by HPLC. In the first study, Ao-LABL was mixed with HA in acetate buffered saline. For reference, the number of reactive sites per mole of HA was calculated by dividing the mean molecular weight of HA by the monomer unit MW (Table 1).

TABLE 1

| Mean HA MW (Da) | Monomer unit MW (Da) | # amide sites per Mole of HA |
|---|---|---|
| 31,000 | 417 | 74.3* |

*Indicates the number of amide sites. For reference, there are an equal number of carboxylic acid sites.

After the designated reaction time, the product was extensively dialyzed to remove any unreacted free peptide. The conjugate product and the dialysate were lyophilized and the reaction efficiency was determined by reversed-phase HPLC. The mass of unreacted peptide in the dialysate was compared to the mass of peptide conjugated to the HA. Grafted Ao-LABL was hydrolyzed from the conjugate prior to analysis using buffer at pH 2 (Table 2). A reaction efficiency of 64% was achieved at 8 hours reaction time. By extending the reaction time from 8 hours to 16 hours and maintaining the buffer at 20 mM acetate, a reaction efficiency of ~95% was achieved (Table 2).

TABLE 2

| Sample | Area Under Curve | Total Area of Peaks |
|---|---|---|
| Ao-LABL Peptide | 8799141 | 8799141 |
| HA conjugate (8 hr)* | 5633361 | 8774823 |
| Dialysis Solution (8 hr)** | 3141462 | |
| HA conjugate (16 hr)* | 8421520 | 8421520 |
| Dialysis Solution (16 hr)** | Not detected | |
| Reaction Efficiency | | 96% at 16 hrs |

*Peptide was first hydrolyzed from HA at pH 2
**Unreacted peptide in dialysate

In addition to analyzing the peptide concentration hydrolyzed from the HA, the change in size of the conjugate product was also analyzed by Gel Permeation Chromatography (GPC) and compared to different molecular weights of HA (FIG. 7). The conjugate product showed an increase in relative molecular weight as indicated by the shift to a smaller retention volume. The peak width remained relatively constant suggesting that the polydispersity of HA did not substantially change after conjugation. Thus, the peptide graft density may have been similar on each HA chain.

Next, the simultaneous conjugation of two aminooxy-peptides was investigated. Equal moles of Ao-LABL and Ao-PLP were added to HA and the reaction was carried out for 16 hours. After extensive purification by dialysis and lyophilization of the product, the peptides were cleaved from HA and analyzed by HPLC to determine the mole percent of each peptide on the HA backbone. Both peptides were grafted to HA at nearly an equimolar ratio (Table

TABLE 3

| Peptide | Concentration (nmol) | mol % |
|---|---|---|
| Ao-LABL | 650 | 54 |
| Ao-PLP | 550 | 46 |

The stability of the N-oxime bond between the peptide and HA polymer was also investigated by challenging the conjugate with different pH buffer conditions. Previous studies involving oxime bonds resulting from the reaction of aminooxy groups with aldehydes or ketones have shown that the oxime bond is labile to both acid and based catalyzed hydrolysis. The rate of hydrolysis was pH dependent at high and low pH; however, the rate becomes independent of pH between pH 5-8. The stability of the synthesized HA-peptide conjugates was evaluated across a pH range of 2-7.5 by putting the dissolved conjugate into three different pH buffer conditions and measuring the peptide released into solution. The released peptide hydrolyzed from the HA backbone was quantified by HPLC over the course of 300 minutes. Conjugates at pH 5.5 and 7.5 reached an apparent equilibrium by 240 minutes with a total of 10% of peptide hydrolyzed from the conjugate. At pH 2, 100% of the peptide was hydrolyzed after only 60 minutes (FIG. 8).

EXAMPLE 2

Materials and Methods

Materials. HA, with an average molecular weight of 31 kD was purchased from Lifecore. Analytical grade acetonitrile and synthesis grade TFA were purchased from Fisher Scientific. Research grade sodium acetate, acetic acid, and D$_2$O were purchased from Sigma. Water was provided by a Labconco Water PRO PS ultrapure water purification unit. Poly (DL-lactic-co-glycolic acid) (50:50) (PLGA; inherent viscosity of 1.05 dL/g, Mw ~101 kDa) was purchased from LACTEL Absorbable Polymers International (Pelham, Ala., USA). Pluronic® F68 (Mw ~8.4 kD) and Pluronic® F108 (Mw ~14.6 kD) were obtained from BASF Corporation. Acetone, diethyl ether and 1× Tris/EDTA buffer solution (pH 8) were obtained from Fisher Scientific. D-mannitol, Dess-Martin periodianine, tert-butyl carbazate (TBC), trinitrobenzenesulfonic acid (TNBS), dichloromethane anhydrous (DCM) and Triton X-100 were purchased from Sigma-Aldrich.

Peptide Synthesis.

Aminooxy peptides were synthesized using 9-fluorenylmethyloxycarbonyl-protected amino acid chemistry on polyethylene glycol-polystyrene resins. The peptides synthesized were aminooxy-LABL (aminooxy-ITDGEATDSG, Ao-LABL), a ligand of ICAM-1 and aminooxy-PLP (aminooxy-HSLGKWLGHPDKF, Ao-PLP), an antigen derived from proteolipid protein amino acids 139-151 ($PLP_{137-151}$). Peptides were deprotected, cleaved from resin, and isolated by precipitation in ether. Purification was completed using preparatory HPLC followed by lyophilization. Peptide identity was verified and purity/content was assessed using Mass Spectroscopy and analytical HPLC. BPI, which is a fusion of PLP and LABL, was synthesized and purified as previously reported (HS KINIG 1-IPDKF-AcGAcGAc-ITDGEATDSG).

Reaction of Aminooxy Peptides to Polymers.

HA was dissolved in 20 mM Acetate buffer (pH 5.5+0.1 pH units) and aminooxy reactive peptide(s) added. When both LABL and PLP peptides were used, each was weighed separately, and then added simultaneously. After addition of the peptide(s), the reaction solution pH was adjusted back to pH 5.5±0.1 pH units. Reaction solutions were stirred at 500 RPM using magnetic stir bars for ~16 hr. After the reaction, the soluble antigen array (SAgA) product was purified by extensive dialysis to remove any unreacted peptide, and then lyophilized.

Gel Permeation Chromatography.

The relative molecular weight of the HA and of the SAgAs was estimated using a Viscotek GPC max VE 2001 GPC solvent/sample module, VE 3580 refractive index detector, and 270 Dual Detector with right angle light scattering. A tandem column setup of two Viscogel GMPWx1 columns (Viscotek) was used at a flow rate of 1 mL/min with isocratic elution in water for 30 min.

High Performance Liquid Chromatography.

Quantification of free peptide post reaction was accomplished by gradient reversed phase HPLC (SHIMADZU) using a Vydac HPLC protein and peptide C18 column. HPLC system was composed of an SCL-20A SHIMADZU system controller, LC-10AT VP SHIMADZU liquid chromatograph, SIL-10A XL SHIMADZU auto-injector set at 75 μL injection volume, DGU-14A SHIMADZU degasser, sample cooler, and SPD-10A SHIMADZU UV-vis detector (220 nm). A personal computer equipped with SHIMADZU class VP software controlled the HPLC-UV system. Gradient elution was conducted at constant flow of 1 mL/min, from 100% A to 35% A (corresponding to 0% B to 65% B) over 50 min, followed by an isocratic elution at 75% B for 3 min. Mobile phase compositions were (A) acetonitrile-water (5:95) with 0.1% TFA and (B) acetonitrile-water (90:10, v/v) with 0.1% TFA. At the completion of each analysis, the cartridge was equilibrated at initial conditions at 1 mL/min flow rate for 5 min with A.

Results

Characterization of Polymeric Soluble Antigen Arrays.

GPC and HPLC were employed to observe any change in retention time resulting from the presence of peptides grafted to the HA. When analyzed by GPC, the product showed a decrease in retention time suggesting an increase in molecular weight relative to the HA (FIG. 7). To quantify the amount of peptide grafted to the polymer, the product retentate and dialysate (containing unreacted peptide) were analyzed by HPLC after extensive dialysis. The product retentate was incubated at room temperature in pH 2 mobile phase buffer. At this pH, the N-oxime bond is rapidly hydrolyzed, thus allowing quantification of the peptide released from the product. Typical chromatograms showed the presence of the Ao-LABL peptide, the Ao-PLP peptide, or both (FIG. 11A). The dialysate showed no peaks. Any unreacted peptide was below the limit of detection of the HPLC (FIG. 11B). A 1:1 ratio of the peptides was achieved. Any difference in peak intensities was primarily due to the different absorption coefficients of these peptides. Data for all the SAgA types suggested highly efficient grafting (Table 4).

TABLE 4

| Sample | LABL Conc (nMol) | PLP Conc (nMol) | Final Ratio |
|---|---|---|---|
| $SAgA_{LABL-PLP}$ | 325 | 275 | 1.2:1 |
| $SAgA_{LABL}$ | 462 | — | n/a |
| $SAgA_{PLP}$ | — | 286 | n/a |

EXAMPLE 3

Materials

All materials were purchased from Sigma-Aldrich (St. Louis, Mo., USA) unless otherwise stated. 1H,H-perfluoro-N-octyl acrylate was purchased from ExFluor Research Corporation (Round Rock, Tex., USA). Vazo-52 was purchased from DuPont (Wilmington, Del., USA). Prior to nanoparticle synthesis (1,5-N-vinylformamido) ethyl ether was prepared as previously described. Impurities were precipitated out of N-vinyl formamide (NVF) using absolute ethanol and vacuum filtered prior to use. All other reagents were used as received.

Nanoparticle Synthesis.

Nanoparticles were synthesized using a free radical polymerization technique. First, 10 mL of 1H,H-perfluoro-n-octyl acrylate, 3.5 mL of NVF, 7 mL of (1,5-N-vinylformamido) ethyl ether, and 0.005 g of (E)-2,20-(diazene-1,2-diyl)bis(2, 4-dimethylpentanenitrile) (Vazo-52) were added to absolute ethanol containing 0.018 $g \cdot mL^{-1}$ polyvinylpyrrolidone (PVP, Mw ~360 kDa). The reagent mixture was sparged for 10 min with argon to remove dissolved oxygen, then heated in a silicone oil bath to 50° C. and stirred at ~900 rpm. The reaction was carried out under an argon atmosphere for 24 h. The product was then dialyzed against deionized water using a 1 kDa MWCO regenerated cellulose ester dialysis tube for 24 h. The dialysate was changed five times to ensure complete solvent exchange. Particle suspensions were then centrifuged twice at 15,000 rpm for 45 min. The pellet was collected each time and resuspended in deionized water.

Characterization of Nanoparticles.

The size and zeta potential of the nanoparticles were determined using DLS dynamic light scattering (DLS; ZetaPals, Brookhaven Instruments). All measurements were taken five times. Measurements are reported as the mean±standard uncertainty. ESEM experiments were performed using an FEI Quantafield emission ESEM. All calculations were done using Image Pro software. Samples were prepared by decanting a small volume of nanoparticles suspended in deionized water onto a polished silicon wafer and allowing the water to evaporate under a fume hood. Samples were sputter coated with 5 nm of gold prior to imaging. All samples were analyzed using an acceleration voltage of 10 keV under high vacuum.

Time-of-Flight Secondary Ion Mass Spectrometry (TOF-SIMS).

TOF-SIMS was used to analyze the surface chemistry of the nanoparticles (Ion-TOF IV). Samples were prepared by decanting a small volume of nanoparticles suspended in deionized water onto a polished silicon wafer and allowing the water to evaporate under a fumehood. TOF-SIMS experiments were performed on an Ion-TOF IV instrument equipped with both Bi ($Bi^+_n$, where n=1-7) and $SF^+5$ primary ion beam cluster sources. The analysis source was a pulsed, 25 keV bismuth cluster ion source (Bi '3), which bombarded the surface at an incident angle of 45° to the surface normal. The target current was maintained at ~0.3 pA (±10%) pulsed current with a raster size of 200 µm×200 µm for all experiments. Both positive and negative secondary ions were extracted from the sample into a reflectron-type time of flight mass spectrometer. The secondary ions were then detected by a microchannel plate detector with a postacceleration energy of 10 kV. A low energy electron flood gun was utilized for charge neutralization in the analysis mode. Each spectrum was averaged over a 60 s time period, with a cycle time of 100 µs. These conditions resulted in accumulated $Bi^+_3$ ion doses that were well below $10^{13}$ ions.$cm^{-2}$.

Fourier Transform Infrared (FTIR) Reflection Spectroscopy.

FTIR spectroscopy was used to qualitatively determine the identity of functional groups present within the nanoparticles (Smiths Illuminate FTIR Microscope). All experiments were done on a diamond attenuated total reflectance objective microscope accessory. Reported spectra are the average of 128 scans.

Solid-State $^{19}$F-NMR Spectroscopy.

The solid-state NMR (ssNMR) spectra were obtained on a 3-channel Tecmag spectrometer operating at 284.0 MHz for $^{19}$F and 301.9 MHz for $^1$H using an $^1$H/$^{19}$F probe. The sample was packed in a 4 mm zirconia rotor with Torlon endcaps and Vespel drivetips and spun at 10,000 kHz. The NMR spectrum was obtained using H-F cross polarization and a sweep width of 100 kHz. A total of 1024 scans were obtained with a dwell time of 10 µs. The chemical shift reference was set at −121.1 ppm using Teflon. Interference from the Teflon endcaps was not subtracted because it was negligible under these conditions.

Results and Discussion

Particles were synthesized using a single step, free radical polymerization method and then precipitated in water. In this method, NVF, (1,5-N-vinylformamido) ethyl ether, and 1H,H-perfluoro-n-octyl acrylate were added to a solution of PVP in ethanol (FIG. 12). Vazo52 was added as an initiator, and the solution was sparged with argon. The reaction was carried out at 50° C. for 24 h. Particles were prepared without PVP under the same conditions to serve as a control group. These particles were larger than the particles prepared in the presence of PVP and were not used in further analysis. The product was then dialyzed against deionized water to induce particle precipitation, and then centrifuged and resuspended twice in water (FIG. 12).

The nanoparticles had a size distribution with maxima at 250 and 700 nm according to DLS. After adding Tween-20 (final concentration: $5.0×10^{-4}$ g·$mL^{-1}$) and sonicating for 4 h, the distribution maxima shifted to 250 and 575 nm (FIG. 13). ESEM imaging suggested that the particles were substantially smaller than 500 nm (FIG. 13). An analysis of the ESEM image (FIG. 13A, top image) using Image-Pro software revealed a mean particle size of 47.0 nm±3.6 nm (95% confidence level). This disparity between the ESEM and the DLS data could be partially due to swelling of the particles in aqueous medium, but is most likely due to flocculation occurring in water, which would increase the particle size observed by DLS. This flocculation effect would also explain the bimodality of the DLS results. DLS measurements taken of the product in ethanol after polymerization were indistinguishable from the background, suggesting that the product was soluble. After precipitation in water and solvent exchange, particles demonstrated excellent colloidal stability, and showed only minor settling when left undisturbed at room temperature for more than 5 months. This settling was easily reversed by lightly shaking the vial for several seconds.

FTIR spectroscopy was used to determine the functional groups present in the particles (FIG. 14). The spectra for the nanoparticles showed bands corresponding to both amide I (1670-1650 $cm^{-1}$) and amide III (1315-1250 $cm^{-1}$) peaks. The spectra also showed a second peak in the carbonyl region (1690-1760 $cm^{-1}$), as well as peaks in the ester region (1080-1300 $cm^{-1}$), which were due to the presence of the fluorinated ester group. These peaks were present in the spectra from particles prepared both with and without PVP surfactant, indicating that they originated from the particles themselves and were not solely an artifact from the g-lactam groups present in residual PVP. TOF-SIMS experiments suggested the presence of fluorinated groups on the surface of the particles (FIG. 15A), indicating they would be a suitable agent for cellular imaging applications. SIMS has a sampling depth of −1 nm in polymeric materials, suggesting that some of the fluorinated side chains were present on the surface of the particles. Spectra also indicated the presence of nitrogen-containing groups, which could be from the NVF side chain, the (1,5-N-vinylformamido) ethyl ether crosslinker, or residual PVP surfactant. Regardless of their source, the nitrogen-containing groups provided the particles with a hydrophilic surface character, which may contribute to their aqueous stability. Further, FIG. 24 shows the FTIR spectra of graft polymer products showing new peaks at ~1750 and ~1250 $cm^{-1}$ and loss of the peak at ~1500 $cm^{-1}$ when compared to the HA spectra.

The presence of fluorinated groups on the surface of the particles could help explain the disparity between the particle sizes measured with DLS and the sizes suggested from the ESEM experiments. The fluorinated groups are extremely hydrophobic, and it is probable that their presence on the particles' surface would induce flocculation due to hydrophobic interactions. This phenomenon would be in competition with the repulsive effects of the hydrophilic groups on the particles' surface. DLS experiments showed changes in measured particle size as particle concentration was varied, which suggests that flocculation was occurring (FIG. 13). Additionally, sonication and the addition of Tween-20 (final concentration: $5.0×10$-4 g·$mL^{-1}$) were shown to decrease the effect of flocculation.

Solid-state $^{19}$F-NMR (ssNMR) was used to help further elucidate the structure of the particles and validate their use as MRI contrast agents (FIG. 15B). The locations of the peaks were consistent with the presence of two different fluorine-containing sites within the fluorinated group. The peak at −82.1 ppm originates from $CF_3$ fluorine and the one at −122.8 from $CF_2$ fluorine, which is overlapped with spinning sidebands. This is consistent with the structure of the 1H,H-perfluoro-n-octyl acrylate monomer. The spectrum suggests that in vivo studies will require selective excitation due to the different fluorine chemical shifts present in the particles.

EXAMPLE 4

Materials

All materials were purchased from Sigma-Aldrich unless otherwise stated. 1H,H-perfluoro-n-octyl acrylate was purchased from ExFluor Research Corporation (Round Rock, Tex.). (E)-2,2'-(diazine-1,2-diyl)bis(2,4-dimethylpentanenitrile) (Vazo-52) was purchased from DuPont (Wilmington, Del.). Dialysis membranes were purchased from Spectrum Labs (Rancho Dominguez, Calif.). Prior to nanoparticle synthesis, (1,5-N-vinylformamido) ethyl ether was synthesized as previously described. (Shi, L. J. 2007; Shi, L. J. 2008) Impurities were precipitated out of N-vinyl formamide using absolute ethanol and vacuum filtered prior to use. All other reagents were used as received.

Methods

Fluorinated-Fluorescent Nanoparticle Synthesis.

NPs were synthesized using a free radical polymerization method similar to one described previously. First, 20 μL, of 1H,H-perfluoro-n-octyl acrylate, 20 μL, of (1,5-N-vinylformamido) ethyl ether and 20 μL, of NVF were dissolved in absolute ethanol containing 0.015 g/mL PVP as a surfactant (MW approximately 360 kDa). Next, 0.0055 mg of fluorescein-O-acrylate and 0.0076 mg of Vazo-52 initiator were added to the solution under stirring. The reagent mixture was then sparged with nitrogen for 10 minutes to remove dissolved oxygen, then was heated in a silicone oil bath to 60° C. and stirred. The reaction was carried out isothermally under a nitrogen atmosphere for 24 hours. The reaction vessel was protected from ambient light to minimize photobleaching of the fluorescent monomer. The product was then dialyzed against deionized water using a 500 Da molecular weight cut off (MWCO) regenerated cellulose ester dialysis tube for 24 hours. The dialysate was changed at least 5 times to ensure complete solvent exchange and the removal of unreacted fluorescein-O-acrylate monomer. The resultant nanoparticle suspension was then purified by centrifugation for 1 hour at 18,000 rpm. Each centrifugation cycle was repeated at least 3 times. Particles were then flash-frozen in liquid nitrogen and lyophilized.

Aminooxylated LABL Peptide Synthesis.

Aminooxy peptides were synthesized using 9-fluorenylmethyloxycarbonyl-protected amino acid chemistry on polyethylene glycol-polystyrene resins. The peptides synthesized where aminooxy LABL (aminooxy-ITDGEATDSG), an ICAM-1 antagonist. Peptides were deprotected, cleaved from resin, and isolated by precipitation in ether.

Purification was completed using preparatory HPLC, followed by lyophilization. Peptide identity was verified and purity/content was assessed using analytical HPLC and mass spectroscopy.

Conjugation of Aminooxylated LABL Peptide to Fluorinated-Fluorescent NPs.

For the conjugation step, 5.9 mg of NPs were re-suspended in 5.9 mL of 20 mM acetate buffer, to a final concentration of 1 mg/mL. Particles were then sonicated for 10 minutes to disperse the suspension. A volume of 3 mL (approximately 3 mg of nanoparticles) was transferred to a separate reaction flask, to which 21.43 mg of aminooxy-LABL (aminooxy-ITDGEATDSG) was added and dissolved by stirring. The pH of both the nanoparticle (NP) solution and LABLconjugated NP solution (LABL-NPs) was measured and adjusted to pH 5.5. Reaction flasks were stirred at 500 RPM for 16 hours. Reaction time was based on previously conducted studies. After the reaction, the solution was extensively dialyzed against deionized H2O (MWCO 3500 Da) to remove unreacted peptide, followed by lyophilization of the dialyzed product.

Up-Regulation of ICAM-1 by Tumor Necrosis Factor-a (TNF-a).

HUVEC cells (4.5×105 cells in 80 l of serum free F 12K medium) were stimulated using 1,000 U/ml of TNF-a for 24 hrs. Cells at the same concentration were not activated and used as a control. HUVEC cells, with or without ICAM-1 upregulation, were incubated with 5% bovine serum albumin (BSA) in phosphate buffered saline (PBS) for 10 min at 4 C and then anti-ICAM-1-FITC (0.05 mg/ml) was added to cells and incubated at 4° C. for 45 min. Free antibodies were removed by rinsing three times with PBS after centrifugation (4,000 RPM, 3 min). The fluorescence intensity of the cells was analyzed by flow cytometry. Data analysis was performed using Cell Quest software (BD).

Binding and Uptake of LABL-NPs by HUVEC Cells.

The binding and uptake of LABL-NPs was studied by using fluorescence spectroscopy. TNF-a stimulated HUVEC cells (5×105 cells/ml) were added in a 96 well-plate (100 l/well) and incubated with LABL-NPs or NPs (3.7 mg/ml, 30 l) at 37 C for 5, 15, 30 and 60 min and washed with PBS. The fluorescence intensity of cells was measured using a fluorescence plate reader (Spectramax M5; ex., 450 nm; em., 500 nm).

Statistical Analysis.

Statistical evaluation of data was performed using an analysis of variance (single-factor ANOVA). Tukey's test was used as a post hoc analysis to assess the significance of differences. A value of $p<0.05$ was accepted as significant.

Results

Preparation of Fluorinated-Fluorescent Nanoparticles.

In this example, fluorinated-fluorescent nanoparticles were synthesized and evaluated as a potential multimodal in vitro imaging probe for optical fluorescence and SIMS imaging (FIG. 16). Fluorine was selected as a SIMS imaging medium because of its biological rarity and high ion yield in SIMS. Fluorinated-fluorescent nanoparticles were prepared using a free radical polymerization method, similar to what has been described previously. (Bailey, M. M. 2010) NPs were conjugated with aninoxyLABL peptide using an N-oxime formation strategy. DLS showed a mean particle diameter of 440 nm±4.3 nm for the unconjugated NPs and 354 nm±10 nm for the LABLNPs (Table 5).

TABLE 5

| | Diameter (nm) | Polydispersity | Zeta Potential (mV) |
|---|---|---|---|
| NP | 440 ± 4.3 | 0.21 ± 0.019 | −5.08 ± 0.86 |
| LABL-NP | 354 ± 10 | 0.167 ± 0.083 | −10.03 ± 3.27 |

The polydispersities for the particle samples were 0.21±0.019 for the unconjugated NPs and 0.167±0.083 for the LABL-NPs, and the measured zeta potentials were 5.08 mV±0.86 mV and −10.03 mV±3.27 mV for the unconjugated NPs and the LABL-NPs, respectively. The observed decrease in NP size after conjugation with the LABL peptide could be due to increased colloidal stability arising after conjugation due to the increased surface charge magnitude, which results from the presence of anionic amino acid residues in the LABL peptide. Fluorinated groups on the NPs surface would be extremely hydrophobic, which might cause agglomeration, and hence an increased observed particle size for the unconjugated NPs. Presumably these hydrophobic interactions are mitigated by the presence of the LABL peptide, which decreases the tendency of the NPs to agglomerate and hence the observed particle size.

Binding and Uptake of Nanoparticles in Cells.

Proinflammatory cytokines such as TNF-a have previously been shown to upregulate the expression of ICAM-1. HUVEC cells were incubated with 1,000 U/ml of TNF-a for 24 hrs to induce overexpression of ICAM-1. HUVEC cells, with or without ICAM-1 upregulation, were incubated with anti-ICAM-1-FITC, which resulted in an increase in ICAM-1 expression compared to HUVEC cells incubated in medium without TNF-a. The result confirmed the overexpression of ICAM-1 and validated the use of this cell line for this study.

NPs conjugated with LABL peptide were rapidly taken up by HUVEC cells, as determined by fluorescence measurements after incubation for several time points (FIG. 17). The normalized fluorescence intensity of the LABL-NPs was approximately 30 times greater after any incubation time (5 min to 60 min) than the normalized fluorescence intensity of the non-conjugated NPs, most likely due to binding to ICAM-1, which was facilitated by the LABL peptide. The enhanced binding of nanoparticles to ICAM-1 mediated through LABL and similar peptides has been described by others.

EXAMPLE 5

Methods 4.5 µMol of NAG was added to 1 mL 20 mM acetate buffer pH 5.5. Once dissolved, 4.5 µMol Ao-PLP peptide was added. The solution was mixed for 16 hours at room temperature. After reaction, the solution was lyophilized and product was stored at −20 C. The reaction is shown below:

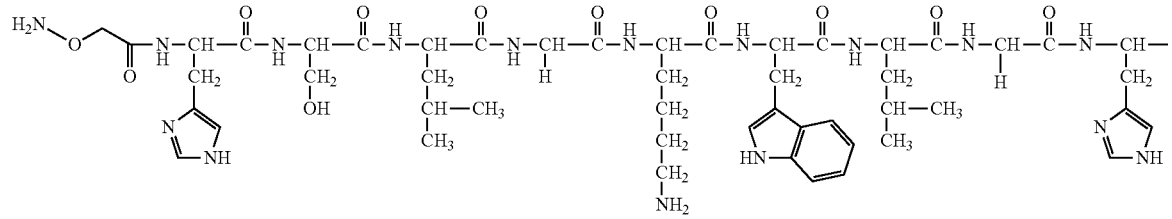

Results

Mass spec results show product peaks at 1821 and 1798 (with and without sodium as illustrated in FIGS. 18A-18B) for reaction of NAG and Ao-peptide. The proposed product structures are as follows:

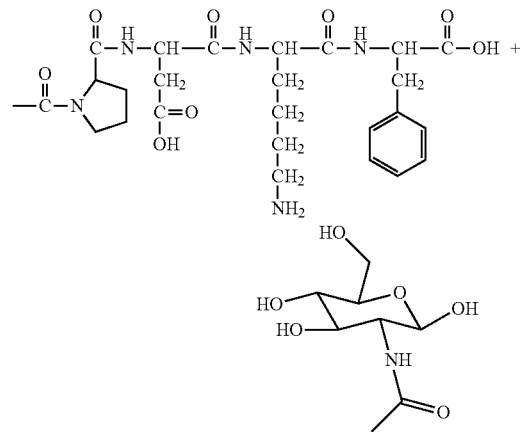

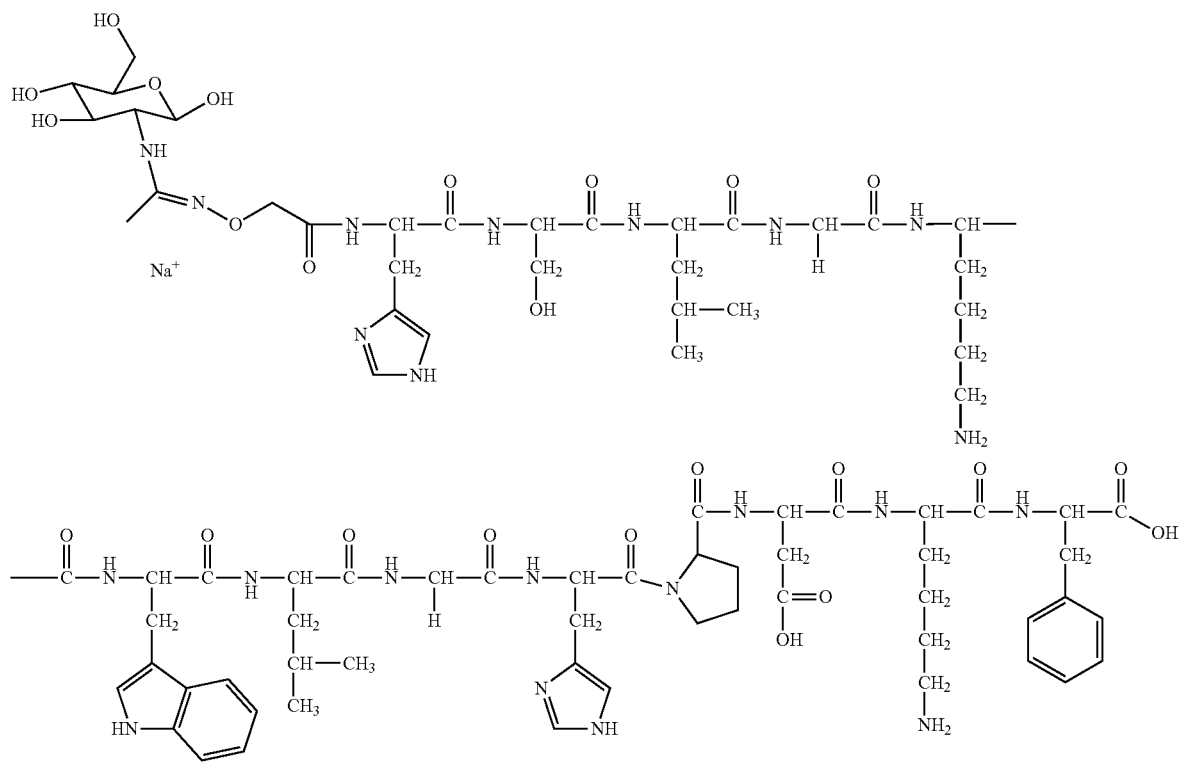
Molecular Weight: 1820.95
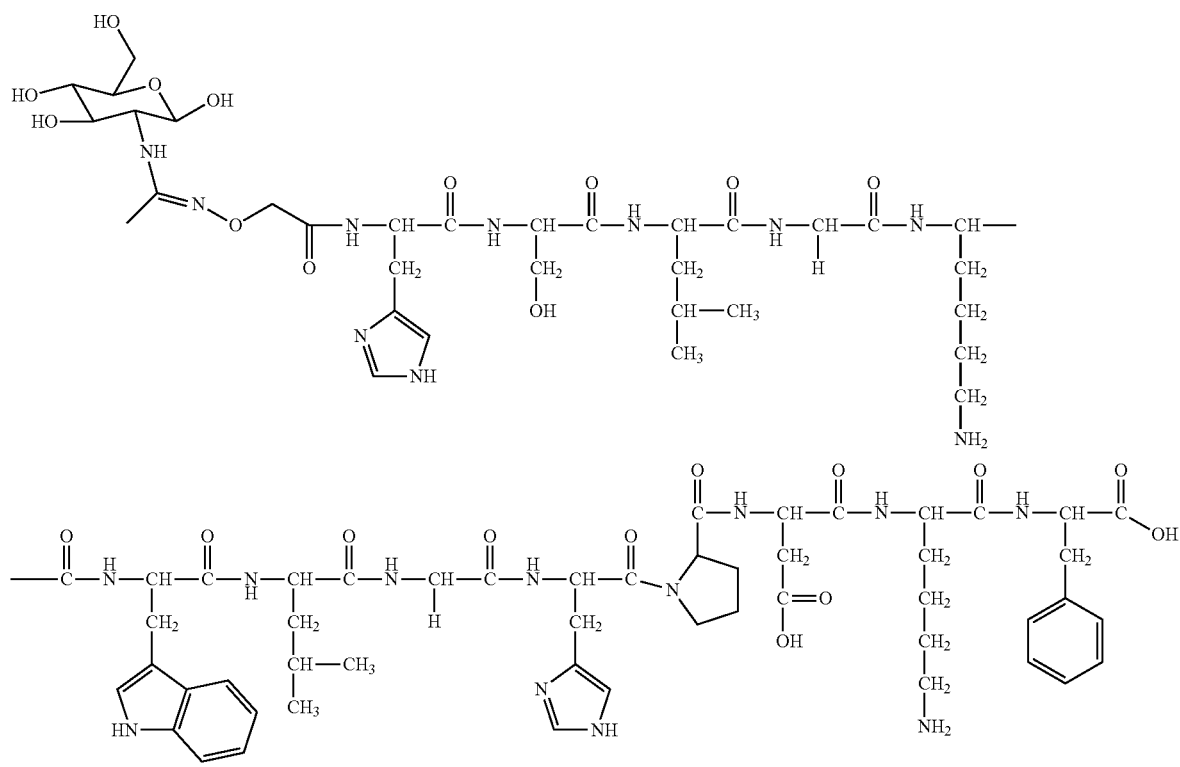
Molecular Weight: 1797.96

EXAMPLE 6

Methods 4.5 μMol of NAG was added to 1 mL 20 mM acetate buffer pH 5.5. Once dissolved, 4.5 μMol Ao-IBR peptide was added. The solution was mixed for 16 hours at room temperature. After reaction, the solution was lyophilized and product was stored at −20 C. The reaction is shown below:

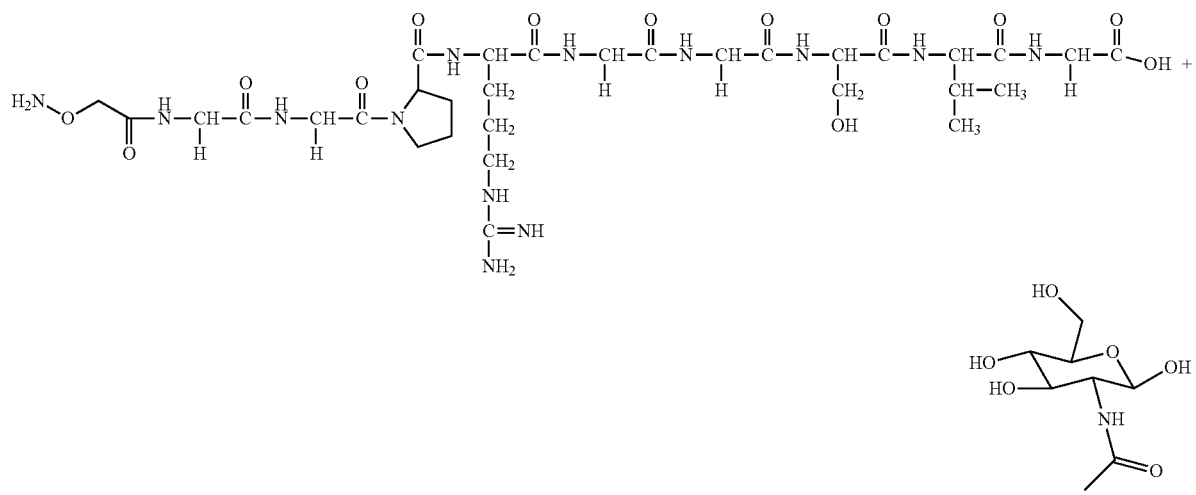

Results

Mass spec results show product peaks at ~1042 and ~1018 (with and without sodium as illustrated in FIGS. 19A-19B) for reaction of NAG and Ao-IBR. The proposed product structures are as follows:

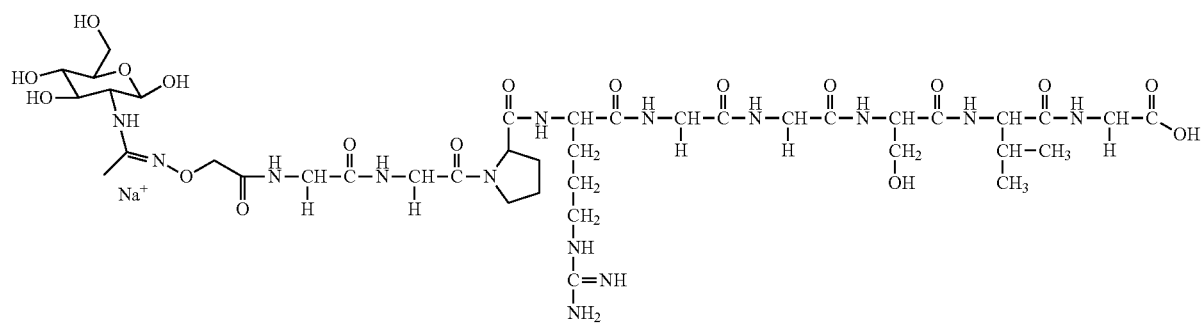

Molecular Weight: 1042.01

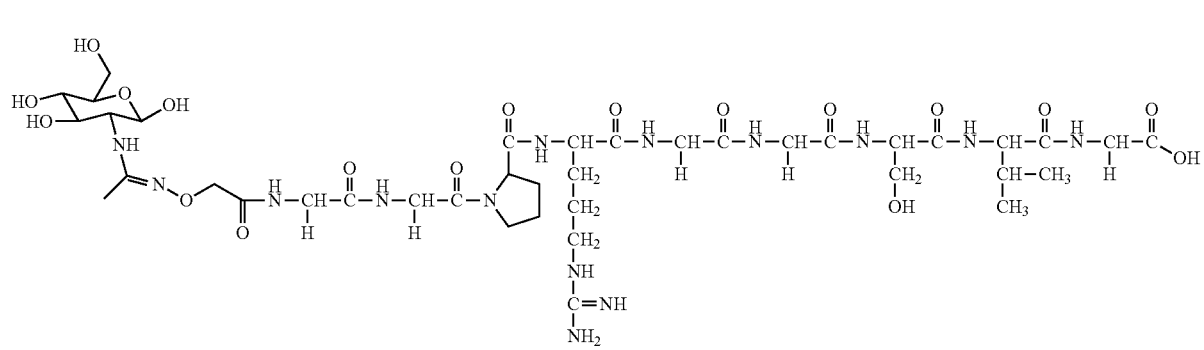

Molecular Weight: 1019.02

EXAMPLE 7

Methods

The following polymers and probes were used in this example:

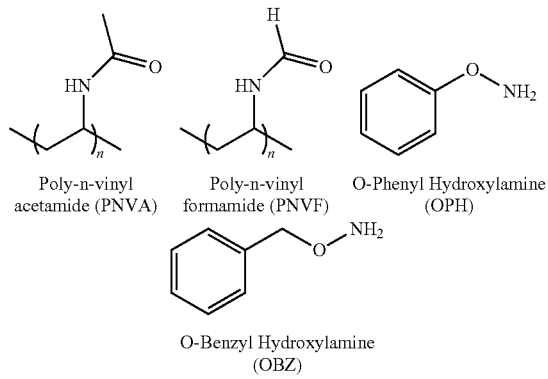

Poly-n-vinyl acetamide (PNVA)  Poly-n-vinyl formamide (PNVF)  O-Phenyl Hydroxylamine (OPH)

O-Benzyl Hydroxylamine (OBZ)

A 2 mg/mL solution of polymer in 20 mM acetate buffer at pH 5.5 was prepared. Aminooxy-reactive probes in a 1:2 molar ratio were added to available reactive sites on polymer. The reaction mixture was stirred at 400 rpm for 24 hours. After the reaction, the products were purified by dialysis using MWCO dialysis tubing appropriate for polymer size. The dialysis wash should be 100× the reaction volume. Dialysis was performed for 24 hours changing dialysis solution at least 3 times. Dialyzed product was lyophilized. HPLC was performed on the resultant products.

HPLC results at 280 nm for addition of OPH to PNVF or PNVFA polymers in acetate buffer pH 5.5 for 24 hours are shown in Table 6 below.

TABLE 6

|  | 280 nm Abs (mAU) Polymer | 280 nm Abs (mAU) Polymer + Probe | Change in Abs (mAU) |
|---|---|---|---|
| Poly-n-vinyl formamide | 199863 | 352306 | 152443 |
| Poly-n-vinyl acetamide | 32029 | 690884 | 658885 |

An HPLC chromatogram at 280 nm comparing PNVF starting material with PNVF reacted with OPH in acetate buffer pH 5.5 for 24 hours is shown in FIG. 20. Shift in retention time to earlier time point indicates increase in hydrophobicity. (FIG. 20). HPLC chromatogram at 280 nm comparing PNVFA starting material with PNVFA reacted with OPH in acetate buffer pH 5.5 for 24 hours is shown in FIG. 21. Shift in retention time to earlier time point indicates increase in hydrophobicity. Table 7 below shows HPLC results at 280 nm for addition of OBZ to PNVF or PNVFA polymers in acetate buffer pH 5.5 for 24 hours.

TABLE 7

|  | 280 nm Abs (mAU) Polymer | 280 nm Abs (mAU) Polymer + Probe | Change in Abs (mAU) |
|---|---|---|---|
| Poly-n-vinyl formamide | 199863 | 1229323 | 1029460 |
| Poly-n-vinyl acetamide | 32029 | 70078 | 38049 |

HPLC chromatogram at 280 nm comparing PNVF starting material with PNVF reacted with OBZ in acetate buffer pH 5.5 for 24 hours is shown in FIG. 22. Shift in retention time to earlier time point indicates increase in hydrophobicity. HPLC chromatogram at 280 nm comparing PNVFA starting material with PNVFA reacted with OBZ in acetate buffer pH 5.5 for 24 hours is shown in FIG. 23. Shift in retention time to earlier time point indicates increase in hydrophobicity.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

REFERENCES

Aharoni, R., D. Teitelbaum, et al. (2000). "Specific Th2 cells accumulate in the central nervous system of mice protected against experimental autoimmune encephalomyelitis by copolymer 1." Proc Natl Acad Sci USA 97(21): 11472-11477.

Ahmed, N. and S. Gottschalk (2009). "How to design effective vaccines: lessons from an old success story." Expert Rev Vaccines 8(5): 543-546.

Bailey, M. M.; Mahoney, C. M.; Dempah, K. E.; Davis, J. M.; Becker, M. L.; Khondee, S.; Munson, E. J.; Berkland, C., Fluorinated Copolymer Nanoparticles for Multimodal Imaging Applications. Macromolecular Rapid Communications 2010, 31, (1), 87-92.

Bollyky, P. L., J. D. Lord, et al. (2007). "Cutting edge: high molecular weight hyaluronan promotes the suppressive effects of CD4+CD25+ regulatory T cells." J Immunol 179(2): 744-747.

Bromley, S. K., A. Iaboni, et al. (2001). "The immunological synapse and CD28-CD80 interactions." Nat. Immunol. 2(12): 1159-1166.

Bullard, D. C., X. Hu, et al. (2007). "p150/95 (CD11c/CD18) expression is required for the development of experimental autoimmune encephalomyelitis." Am J Pathol 170(6): 2001-2008.

Bullard, D. C., X. Hu, et al. (2007). "Intercellular adhesion molecule-1 expression is required on multiple cell types for the development of experimental autoimmune encephalomyelitis." J Immunol 178(2): 851-857.

Byers, M. A., P. A. Calloway, et al. (2008). "Arrestin 3 mediates endocytosis of CCR7 following ligation of CCL19 but not CCL21." J Immunol 181(7): 4723-4732.

Cai, S., Y. Xie, et al. (2008). "Intralymphatic chemotherapy using a hyaluronan-cisplatin conjugate." J Surg Res 147 (2): 247-252.

Cai, S., Y. Xie, et al. (2009). "Pharmacokinetics and disposition of a localized lymphatic polymeric hyaluronan conjugate of cisplatin in rodents." J Pharm Sci.

Cairo, C. W., J. E. Gestwicki, et al. (2002). "Control of multivalent interactions by binding epitope density." J Am Chem Soc 124(8): 1615-1619.

Carter, P. H. and Q. Zhao (2010). "Clinically validated approaches to the treatment of autoimmune diseases." Expert Opin Investig Drugs 19(2): 195-213.

Chittasupho, C.; Xie, S. X.; Baoum, A.; Yakovleva, T.; Siahaan, T. J.; Berkland, C. J., ICAM-1 targeting of doxorubicin-loaded PLGA nanoparticles to lung epithelial cells. Eur J Pharm Sci 2009, 37, (2), 141-50.

Cohen, M. S., S. Cai, et al. (2009). "A novel intralymphatic nanocarrier delivery system for cisplatin therapy in breast cancer with improved tumor efficacy and lower systemic toxicity in vivo." Am J Surg 198(6): 781-786.

Compston, A. and A. Coles (2002). "Multiple sclerosis." The Lancet 359(9313): 1221-1231.

de Sanjose, S., L. Alemany, et al. (2008). "Human papillomavirus vaccines and vaccine implementation." Womens Health (Lond Engl) 4(6): 595-604.

Dintzis, H. M., R. Z. Dintzis, et al. (1976). "Molecular determinants of immunogenicity: the immunon model of immune response." Proc Natl Acad Sci USA 73(10): 3671-3675.

Dintzis, H. M. D., R. Z. (1992). "Profound specific suppression by antigen of persistent IgM, IgG, and IgE antibody production." Proceedings of the National Academy of Sciences 89: 1113-1117.

Dintzis, R. Z., M. H. Middleton, et al. (1983). "Studies on the immunogenicity and tolerogenicity of T-independent antigens." J Immunol 131(5): 2196-2203.

Dintzis, R. Z., B. Vogelstein, et al. (1982). "Specific cellular stimulation in the primary immune response: experimental test of a quantized model." Proc Natl Acad Sci USA 79(3): 884-888.

Dixon, F. J. (1992). Advances in Immunology. San Diego, Academic Press, Inc.

Dustin, M. L. (2002). "The immunological synapse." Arthritis. Res. 4(Suppl 3): S119-125.

Dustin, M. L. (2009). "The cellular context of T cell signaling." Immunity 30(4): 482-492.

Dustin, M. L. and A. S. Shaw (1999). "Costimulation: Building an immunological synapse." Science 283(5402): 649-650.

Fraser, J. R.; Laurent, T. C.; Laurent, U. B. (1997). Hyaluronan: its nature, distribution, functions and turnover. J Intern Med, 242, (1), 27-33.

Gajewiak, J., S. Cai, et al. (2006). "Aminooxy Pluronics: Synthesis and Preparation of Glycosaminoglycan Adducts." Biomacromolecules 7(6): 1781-1789.

Gauthier, M. A. and H. A. Klok (2008). "Peptide/protein-polymer conjugates: synthetic strategies and design concepts." Chem Commun (Camb)(23): 2591-2611.

Gestwicki, J. E., C. W. Cairo, et al. (2002). "Influencing receptor ligand binding mechanisms with multivalent ligand architecture." J Am Chem Soc 124(50): 14922-14933.

Goebel, S., M. Huang, et al. (2005). "VEGF-A Stimulation of Leukocyte Adhesion to Colonic Microvascular Endothelium: Implications for Inflammatory Bowel Disease." Am J Physiol Gastrointest Liver Physiol.

Hartman, N. C., J. A. Nye, et al. (2009). "Cluster size regulates protein sorting in the immunological synapse." Proc Natl Acad Sci USA 106(31): 12729-12734.

Heredia, K. L., Z. P. Tolstyka, et al. (2007). "Aminooxy End Functionalized Polymers Synthesized by ATRP for Chemoselective Conjugation to Proteins." Macromolecules 40(14): 4772-4779.

Hu, X., J. E. Wohler, et al. (2009). "{beta} 2-Integrins in demyelinating disease: not adhering to the paradigm." J Leukoc Biol.

Huang, M., K. Matthews, et al. (2005). "Alpha L-integrin I domain cyclic peptide antagonist selectively inhibits T cell adhesion to pancreatic islet microvascular endothelium." Am J Physiol Gastrointest Liver Physiol 288(1): G67-73.

Hwang, J., R. C. Li, et al. (2007). "Well-defined polymers with activated ester and protected aldehyde side chains for bio-functionalization." J Control Release 122(3): 279-286.

Inobe, J., A. J. Slavin, et al. (1998). "IL-4 is a differentiation factor for transforming growth factor-beta secreting Th3 cells and oral administration of IL-4 enhances oral tolerance in experimental allergic encephalomyelitis." Eur J Immunol 28(9): 2780-2790.

Johnston, C. T., S. L. Wang, et al. (2002). "Measuring the surface area of aluminum hydroxide adjuvant." J Pharm Sci 91(7): 1702-1706.

Kavanaugh, A. F., L. S. Davis, et al. (1996). "A phase I/II open label study of the safety and efficacy of an anti-ICAM-1 (intercellular adhesion molecule-1; CD54) monoclonal antibody in early rheumatoid arthritis." J. Rheumatol. 23(8): 1338-1344.

Kobayashi, N., P. Kiptoo, et al. (2008). "Prophylactic and therapeutic suppression of experimental autoimmune encephalomyelitis by a novel bifunctional peptide inhibitor." Clin Immunol 129(1): 69-79.

Kobayashi, N., H. Kobayashi, et al. (2007). "Antigen-specific suppression of experimental autoimmune encephalomyelitis by a novel bifunctional peptide inhibitor." J Pharmacol Exp Ther 322(2): 879-886.

Kool, M., V. Petrilli, et al. (2008). "Cutting edge: alum adjuvant stimulates inflammatory dendritic cells through activation of the NALP3 inflammasome." J Immunol 181(6): 3755-3759.

Krejcova D, P. M., Safrankova B, Kubala L. (2009). "The effect of different molecular weight hyaluronan on macrophage physiology." Neuro Endocrinol Lett. 30((Suppl)): 106-111.

Krishnamoorthy, G., H. Lassmann, et al. (2006). "Spontaneous opticospinal encephalomyelitis in a double-transgenic mouse model of autoimmune T cell/B cell cooperation." J Clin Invest 116(9): 2385-2392.

Langer-Gould, A. and L. Steinman (2006). "Progressive multifocal leukoencephalopathy and multiple sclerosis: lessons from natalizumab." Curr Neurol Neurosci Rep 6(3): 253-258.

Link, H. (1998). "The cytokine storm in multiple sclerosis." Mult Scler 4(1): 12-15.

Lisak, R. P., B. Zweiman, et al. (1983). "Effect of treatment with Copolymer 1 (Cop-1) on the in vivo and in vitro manifestations of experimental allergic encephalomyelitis (EAE)." J Neurol Sci 62(1-3): 281-293.

Marc A. Gauthier and Harm-Anton Klok (2008). "ChemInform Abstract: Peptide/Protein—Polymer Conjugates: Synthetic Strategies and Design Concepts." ChemInform 39(39).

Matsushita, T., K. Yanaba, et al. (2008). "Regulatory B cells inhibit EAE initiation in mice while other B cells promote disease progression." J Clin Invest 118(10): 3420-3430.

Mempel, T. R., S. E. Henrickson, et al. (2004). "T-cell priming by dendritic cells in lymph nodes occurs in three distinct phases." Nature 427(6970): 154-159.

Miller, S. D., D. M. Turley, et al. (2007). "Antigen-specific tolerance strategies for the prevention and treatment of autoimmune disease." Nat Rev Immunol 7(9): 665-677.

Moriyama, H., K. Yokono, et al. (1999). "Induction of tolerance in murine autoimmune diabetes by transient blockade of leukocyte function-associated antigen-1/intercellular adhesion molecule-1 pathway." J. Immunol. 157: 3737-3743.

Mossman, K. D., G. Campi, et al. (2005). "Altered TCR signaling from geometrically repatterned immunological synapses." Science 310(5751): 1191-1193.

Murray, J. S., S. Oney, et al. (2007). "Suppression of type 1 diabetes in NOD mice by bifunctional peptide inhibitor: modulation of the immunological synapse formation." Chem Biol Drug Des 70(3): 227-236.

Muto J, Y. K., Taylor K R, Gallo R L. (2009). "Engagement of CD44 by hyaluronan suppresses TLR4 signaling and the septic response to LPS" Mol Immunol. 47(2-3): 449-456.

Peek, L. J., C. R. Middaugh, et al. (2008). "Nanotechnology in vaccine delivery." Adv Drug Deliv Rev 60(8): 915-928.

Puffer, E. P., J. K. P., Jessica J. Hollenbeck, John A. Kink, and Laura L. Kiessling. (2006). Activating B Cell Signaling with Defined Multivalent Ligands. ACS Chemical Biology, 2, (4), 8.

Reichardt, P., B. Dornbach, et al. (2007). "The molecular makeup and function of regulatory and effector synapses." Immunol Rev 218: 165-177.

Reim, J. W., D. E. Symer, et al. (1996). "Low molecular weight antigen arrays delete high affinity memory B cells without affecting specific T-cell help." Mol Immunol 33(17-18): 1377-1388.

Reim, J. W. J. (1996). "Low molecular weight antigen arrays delete high affinity memory B cells without affecting specific T-cell help." Molecular immunology 33(1718).

Renee Z. Dintzis, M. O., Marjorie H. Middleton, Gretchen Greene, and Howard M. Dintzis (1989). "The Immunogenicity of Soluble Haptenated Polymers is Determined by Molecular Mass and Hapten Valence." The Journal of Immunology 143(4): 5.

Ridwan, R., P. Kiptoo, et al. (2009). "Antigen-specific Suppression of Experimental Autoimmune Encephalomyelitis by a Novel Bifunctional Peptide Inhibitor: Structure Optimization and Pharmacokinetics." J Pharmacol Exp Ther.

Rolland, J. M., L. M. Gardner, et al. (2009). "Allergen-related approaches to immunotherapy." Pharmacol Ther 121(3): 273-284.

Sant, A. J., F. A. Chaves, et al. (2005). "The relationship between immunodominance, DM editing, and the kinetic stability of MHC class II:peptide complexes." Immunol Rev 207: 261-278.

Schulze-Koops, H., P. E. Lipsky, et al. (1995). "Elevated Th1- or Th0-like cytokine mRNA in peripheral circulation of patients with rheumatoid arthritis. Modulation by treatment with anti-ICAM-1 correlates with clinical benefit." J. Immunol. 155(10): 5029-5037.

Senti, G., B. M. Prinz Vavricka, et al. (2008). "Intralymphatic allergen administration renders specific immunotherapy faster and safer: a randomized controlled trial." Proc Natl Acad Sci USA 105(46): 17908-17912.

Sheridan, C. (2005). "Tysabri raises alarm bells on drug class." Nat Biotechnol 23(4): 397-398.

Shi, L. J.; Berkland, C., Acid-labile polyvinylamine micro- and nanogel capsules. Macromolecules 2007, 40, (13), 4635-4643.

Shi, L. J.; Khondee, S.; Linz, T. H.; Berkland, C., Poly-N-vinylformamide) nanogels capable of pH-sensitive protein release. Macromolecules 2008, 41, (17), 6546-6554.

Shuang, C., X. Yumei, et al. (2008). "Intralymphatic Chemotherapy Using a Hyaluronan-Cisplatin Conjugate." The Journal of surgical research 147(2): 247-252.

Siliciano R F, C. R., Keegan A D, Dintzis R Z, Dintzis H M, Shin H S. (1985). "Antigen valence determines the binding of nominal antigen to cytolytic T cell clones." J Exp Med 162(2): 768-773.

Stebbings, R., L. Findlay, et al. (2007). ""Cytokine storm" in the phase I trial of monoclonal antibody TGN1412: better understanding the causes to improve preclinical testing of immunotherapeutics." J Immunol 179(5): 3325-3331.

Steinman, L. (2005). "Blocking adhesion molecules as therapy for multiple sclerosis: natalizumab." Nat Rev Drug Discov 4(6): 510-518.

Steinman, L. and P. Conlon (2001). "Antigen specific immunotherapy of multiple sclerosis." J Clin Immunol 21(2): 93-98.

Symer, D. E. D. (1995). "Durable elimination of high affinity, T cell-dependent antibodies by low molecular weight antigen arrays in vivo." Journal of immunology 155(12).

Tesar, B. M., D. Jiang, et al. (2006). "The Role of Hyaluronan Degradation Products as Innate Alloimmune Agonists." American Journal of Transplantation 6(11): 2622-2635.

Vines, C. M., J. W. Potter, et al. (2001) "Inhibition of beta 2 integrin receptor and Syk kinase signaling in monocytes by the Src family kinase Fgr." Immunity 15(4): 507-519.

Vines, C. M., C. M. Revankar, et al. (2003). "N-formyl peptide receptors internalize but do not recycle in the absence of arrestins." J Biol Chem 278(43): 4158141584.

Wei B Y, H.-S. V., Carter B G, Sehon A H. (1984). "Suppression of the anti-trimellityl (TM) IgE response in mice by conjugates of TM with polyvinyl alcohol." Immunology 51(4): 687-696.

Yanaba, K., J. D. Bouaziz, et al. (2008). "B-lymphocyte contributions to human autoimmune disease." Immunol Rev 223: 284-299.

Yanaba, K., J. D. Bouaziz, et al. (2009). "The development and function of regulatory B cells expressing IL-10 (B10 cells) requires antigen receptor diversity and TLR signals." J Immunol 182(12): 7459-7472.

Yanaba, K., Y. Hamaguchi, et al. (2007). "B cell depletion delays collagen-induced arthritis in mice: arthritis induction requires synergy between humoral and cell-mediated immunity." J Immunol 179(2): 1369-1380.

Yednock, T. A., C. Cannon, et al. (1992). "Prevention of experimental autoimmune encephalomyelitis by antibodies against alpha 4 beta 1 integrin." Nature 356(6364): 63-66.

Zhang, N.; Chittasupho, C.; Duangrat, C.; Siahaan, T. J.; Berkland, C., PLGA nanoparticle—peptide conjugate effectively targets intercellular cell-adhesion molecule-1. Bioconjug Chem 2008, 19, (1), 145-52.

What is claimed is:

1. A method comprising:
   providing a first compound comprising at least one reactive amide group;
   providing a second compound comprising at least one reactive aminooxy group; and
   reacting the at least one reactive amide group of the first compound with the at least one reactive aminooxy group of the second compound to form a conjugate comprising the first and second compound.

2. The method of claim 1 wherein:
   the first compound comprises two or more reactive amide groups;
   the second compound comprises two or more reactive aminooxy groups; and
   wherein the two or more reactive amide groups of the first compound and the two or more reactive aminooxy groups of the second compound are reacted to form a crosslinked conjugate.

3. The method of claim 1 wherein:
   the first compound further comprises at least one reactive aminooxy group;
   the second compound further comprises at least one reactive amide group; and
   wherein the first compound and second compound are reacted to form a crosslinked conjugate comprising two or more N-oxime bonds.

4. The method of claim 1 wherein reacting the first compound with the second compound occurs at a pH of from about 4 to about 8.

5. The method of claim 1 wherein reacting the first compound with the second compound occurs at a temperature of from about 20° C. to 30° C.

6. The method of claim 1 wherein the first compound comprises at least one compound selected from the group consisting of: a polymer comprising a reactive amide group, a monomer comprising a reactive amide group, a protein comprising a reactive amide group, a peptide comprising a reactive amide group, a polysaccharide comprising a reactive amide group, a saccharide comprising a reactive amide group, a nucleic acid comprising a reactive amide group and a small molecule comprising a reactive amide group.

7. The method of claim 1 wherein the second compound comprises at least one compound selected from the group consisting of: a polymer comprising a reactive aminooxy group, a monomer comprising a reactive aminooxy group, a protein comprising a reactive aminooxy group, a peptide comprising a reactive aminooxy group, a polysaccharide comprising a reactive aminooxy group, a saccharide comprising a reactive amide group, a nucleic acid comprising a reactive aminooxy group and a small molecule comprising a reactive aminooxy group.

8. A composition comprising a conjugate represented by the following Formula (I):

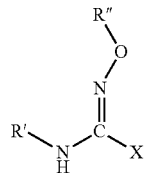

Formula (I)

wherein R' is derived from a compound comprising at least one reactive amide group, R" is derived from a protein or peptide comprising at least one reactive aminooxy group, and X is H, $C_nH_{(n+2)}$.

9. The composition of claim 8 further comprising at least one additional N-oxime bond so as to form a crosslinked composition.

10. The composition of claim 8 wherein R' comprises at least one compound selected from the group consisting of a polymer, a protein, a peptide, a polysaccharide, a saccharide, a nucleic acid and a small molecule.

11. The composition of claim 8 further comprising a pharmaceutically acceptable carrier.

12. The composition of claim 8 wherein the conjugate is a reduced form of Formula I represented by the following Formula (II):

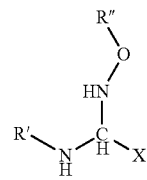

wherein R' is derived from a compound comprising at least one reactive amide group, R" is derived from a protein or peptide comprising at least one reactive aminooxy group, and X is H, $C_nH_{(n+2)}$.

13. A composition comprising a conjugate represented by the following Formula (II):

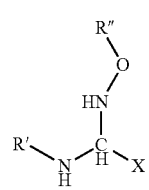

Formula (II)

wherein R' is derived from a compound comprising at least one reactive amide group, R" is derived from a protein or peptide comprising at least one reactive aminooxy group, and X is H, $C_nH_{(n+2)}$.

14. The composition of claim 13 further comprising at least one additional N-oxime bond so as to form a crosslinked composition.

15. The composition of claim 13 wherein R' comprises at least one compound selected from the group consisting of a polymer, a protein, a peptide, a polysaccharide, a saccharide, a nucleic acid and a small molecule.

16. The composition of claim 13 further comprising a pharmaceutically acceptable carrier.

* * * * *